(12) United States Patent
Gierskcky et al.

(10) Patent No.: US 6,492,420 B2
(45) Date of Patent: *Dec. 10, 2002

(54) ESTERS OF 5-AMINOLEVULINIC ACID AS PHOTOSENSITIZING AGENTS IN PHOTOCHEMOTHERAPY

(75) Inventors: Karl E. Gierskcky; Johan Moan; Qian Peng; Harald Steen; Trond Warloe; Alf Bjorseth, all of Oslo (NO)

(73) Assignee: PhotoCure AS, Oslo (NO)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 145 days.

(21) Appl. No.: 09/471,620

(22) Filed: Dec. 21, 1999

(65) Prior Publication Data

US 2001/0051743 A1 Dec. 13, 2001

Related U.S. Application Data

(63) Continuation of application No. 08/913,257, filed as application No. PCT/GB96/00553 on Mar. 8, 1996, now Pat. No. 6,034,267.

(30) Foreign Application Priority Data

| Mar. 10, 1995 | (GB) | 9504948 |
| Dec. 18, 1995 | (GB) | 9525822 |

(51) Int. Cl.[7] ........................ A61K 37/44; C07C 229/06
(52) U.S. Cl. ...................... 514/551; 514/538; 514/863; 514/947; 560/155
(58) Field of Search ................ 514/538, 551, 514/863, 947; 560/155

(56) References Cited

U.S. PATENT DOCUMENTS

| 4,575,515 A | 3/1986 | Sandborn | 514/708 |
| 5,079,262 A | 1/1992 | Kennedy et al. | 514/561 |
| 5,211,938 A | 5/1993 | Kennedy et al. | 424/7.1 |
| 5,219,878 A | 6/1993 | Ringuet et al. | 514/410 |
| 5,234,940 A | 8/1993 | Kennedy | 514/410 |
| 5,422,093 A | 6/1995 | Kennedy et al. | 424/9.61 |
| 5,955,490 A * | 9/1999 | Kennedy et al. | |

FOREIGN PATENT DOCUMENTS

| DE | 2411382 | 9/1975 | |
| EP | 0316179 | 5/1989 | |
| GB | 2058077 A | 4/1981 | C07C/103/52 |
| WO | 91/01727 | 2/1991 | |
| WO | 92/06097 | 4/1992 | C07D/487/22 |
| WO | 92/20810 | 10/1993 | |
| WO | 95/07077 | 3/1995 | A61K/31/195 |

OTHER PUBLICATIONS

Database Xfire, entries 3060978, 5347132, 5499790, 5620924, 5633390, 5991317 and 6517740, Beilstein XP002005286, *chemical Abstracts, 16*, Abstract of Japanese Patent Application No. JP900287712 (Haruhiko), published Jan. 14, 1992, from, (Apr. 16, 1992).
Ariens, E.J., "Drug Design", *Academic Press, New York*, 8–11, 70–71, (1971).
Cotton, F.A., et al., "Advanced Inorganic Chemistry", 5th ed., Wiley, New York, 305–309, 382–386, (1988).
Davies, A.G., "Organic Peroxides", *Butterworth and Co., London*, 196, (1961).
Dougherty, T.J., "Activated Dyes as Antitumor Agents", *Journal of the National Cancer Institute*, 52, 1333–1336, (Apr. 1974).
Kelly, J.F., et al., "Hematoporphyrin Derivative: A Possible Aid in the Diagnosis and Therapy of Carcinoma of the Bladder", *The Journal of Urology*, 115, Coyprighted 1976 by The Williams & Wilkins Co., 150–151, (Feb.).
Kloek, J., et al., "Prodrugs of 5–Aminolevulinic Acid for Photodynamic Therapy", *Photochemistry and Photobiology*, 64(6), 994–1000, (1996).
Morrison, R.T., et al., "Organic Chemistry", 3rd ed., Allyn and Bacon, Boston, 631, 666, 668–9, 673, (1973).*
Qian, P., et al., "A comparison of Different Photosensitizing Dyes with Respect to Uptake C3H–Tumors and Tissues of Mice", *Cancer Letters*, 36, 1–10, (1987).*
Gawell, L., et al., "Synthesis of 5–Substituted 5–Hydroxy–2–pyrrolidones, Metabolites of the Antipsychotic Benzamide Remoxipride", *Acta Chemica Scandinavica*, vol. 43, 7 pages, (1989).
Salerni, O.L., et al., "Synthesis of δ–Aminolaevulinic Acid Analogues as Potential Antimalarial Agents", *J. Chem. Soc. (C)*, 5 pages (1968).
Schulz, G., et al., "3–Imidazoline und $\Delta^3$–Tetrahydropyrimidine durch Termolyse von 3–Oxazolin–5–onen aus N–Acyldipeptiden", *Chem. Ber.*, 113 (2) (5620924), 10 pages, (1980).

* cited by examiner

*Primary Examiner*—Gary Geist
*Assistant Examiner*—Robert W. Deemie
(74) *Attorney, Agent, or Firm*—Kenyon & Kenyon

(57) ABSTRACT

The present invention relates to compounds being esters of 5-aminolevulinic acids or pharmaceutically acceptable salts thereof, including compounds of formula (I) $R_2{}^2N-CH_2COCH_2-CH_2CO-OR^1$ (wherein $R^1$ may represent alkyl optionally substituted by hydroxy, alkoxy, acyloxy, alkoxycarbonyloxy, amino, aryl, oxo or fluoro groups and optionally interrupted by oxygen, nitrogen, sulphur or phosphorus atoms; and $R^2$ represents a hydrogen atom or a group $R^1$, and both $R^2$ groups may be the identical or different), and their use in diagnosis and photochemotherapy of disorders or abnormalities of external or internal surfaces of the body, and products and kits for performing the invention.

9 Claims, 23 Drawing Sheets

Free ALA

ALA methylester 155-20

A

B 156-1

153-11

158-1

159-4

160-1

A

B 162-1

ESTERS OF 5-AMINOLEVULINIC ACID AS PHOTOSENSITIZING AGENTS IN PHOTOCHEMOTHERAPY

CROSS-REFERENCE TO RELATED APPLICATIONS

This application is a continuation of U.S. patent application Ser. No. 08/913,257, filed on Dec. 5, 1997, which in turn is a U.S. national phase filing under 35 USC §371 of International Patent Application No. PCT/GB96/00553 now U.S. Pat. No. 6,034,267, filed on Mar. 8, 1996, which in turn is an international filing of British Patent Application No. 9525822.4, filed on Dec. 18, 1995, and of British Patent Application No. 9504948.2, filed on Mar. 10, 1995, all of which are incorporated herein by reference.

The present invention relates to derivatives of 5-aminolevulinic acid (ALA) and in particular to esters of ALA for use as photosensitizing agents in photochemotherapy or diagnosis.

Photochemotherapy, or photodynamic therapy (PDT) as it is also known, is a recently up-coming technique for the treatment of various abnormalities or disorders of the skin or other epithelial organs or mucosa, especially cancers or pre-cancerous lesions, as well as certain non-malignant lesions for example skin complaints such as psoriasis. Photochemotherapy involves the application of photosensitizing (photochemotherapeutic) agents to the affected area of the body, followed by exposure to photoactivating light in order to activate the photosensitizing agents and convert them into cytotoxic form, whereby the affected cells are killed or their proliferative potential diminished.

A range of photosensitizing agents are known, including notably the psoralens, the porphyrins, the chlorins and the phthalocyanins. Such drugs become toxic when exposed to light.

Photosensitizing drugs may exert their effects by a variety of mechanisms, directly or indirectly. Thus for example, certain photosensitizers become directly toxic when activated by light, whereas others act to generate toxic species, e.g. oxidising agents such as singlet oxygen or other oxygen-derived free radicals, which are extremely destructive to cellular material and biomolecules such as lipids, proteins and nucleic acids. Psoralens are an example of directly acting photosensitizers; upon exposure to light they form adducts and cross-links between the two strands of DNA molecules, thereby inhibiting DNA synthesis. The unfortunate risk with this therapy is that unwanted mutagenic and carcinogenic side effects may occur.

This disadvantage may be avoided by selecting photosensitizers with an alternative, indirect mode of action. For example porphyrins, which act indirectly by generation of toxic oxygen species, have no mutagenic side-effects and represent more favourable candidates for photochemotherapy. Porphyrins are naturally occurring precursors in the synthesis of heme. In particular, heme is produced when iron ($Fe^{3+}$) is incorporated in protoporphyrin IX (Pp) by the action of the enzyme ferrochelatase. Pp is an extremely potent photosensitizer, whereas heme has no photosensitizing effect.

One such porphyrin-based drug, Photofrin, has recently been approved as a photosensitizer in the therapy of certain cancers. The main disadvantage is that since it must be administered parenterally, generally intravenously, cause photosensitization of the skin which may last for several weeks following i.v. injection. Photofrin consists of large oligomers of porphyrin and it does not readily penetrate the skin when applied topically. Similar problems exist with other porphyrin-based photosensitizers such as the so-called "hematoporphyrin derivative" (Hpd) which has also been reported for use in cancer photochemotherapy (see for example S. Dougherty. J. Natl. Cancer Ins., 1974, 52; 1333; Kelly and Snell, J. Urol, 1976, 115: 150). Hpd is a complex mixture obtained by treating haematoporphyrin with acetic and sulphuric acids, after which the acetylated product is dissolved with alkali.

To overcome these problems, precursors of Pp have been investigated for photochemotherapeutic potential. In particular the Pp precursor 5-aminolevulinic acid (ALA) has been investigated as a photochemotherapeutic agent for certain skin cancers. ALA, which is formed from succinyl CoA and glycine in the first step of heme synthesis, is to a limited extent able to penetrate the skin and lead to a localised build-up of Pp; since the action of ferrochelatase (the metallating enzyme) is the rate limiting step in heme synthesis, an excess of ALA leads to accumulation of Pp, the photosensitizing agent. Thus, by applying ALA topically to skin tumours, and then after several hours exposing the tumours to light, a beneficial photochemotherapeutic effect may be obtained (see for example WO91/01727). Since the skin covering basilomas and squamous cell carcinomas is more readily penetrated by ALA than healthy skin, and since the concentration of ferrochelatase is low in skin tumours, it has been found that topical application of ALA leads to a selectively enhanced production of Pp in tumours.

However, whilst the use of ALA represents a significant advance in the art, photochemotherapy with ALA is not always entirely satisfactory. ALA is not able to penetrate all tumours and other tissues with sufficient efficacy to enable treatment of a wide range of tumours or other conditions and ALA also tends to be unstable in pharmaceutical formulations. A need therefore exists for improved photochemotherapeutic agents.

The present invention addresses this need and in particular aims to provide photochemotherapeutic agents which are better able to penetrate the tumour or other abnormality, and which have an enhanced photochemotherapeutic effect over those described in the prior art.

In one aspect, the present invention thus provides compounds being esters of 5-aminolevulinic acids or pharmaceutically acceptable salts thereof for use in photochemotherapy or diagnosis.

In the esters of the invention the 5-amino group may be substituted or unsubstituted, the latter case being the ALA esters.

More particularly, the compounds for use according to the invention are esters of 5-aminolevulinic acids with optionally substituted alkanols, ie. alkyl esters or substituted alkyl esters.

Database Xfire, entries 3060978, 5347132, 5499790, 5620924, 5633390, 5991317, and 6517740 (Beilstein); Cosmo Sogo Kenkyusho KK, Patent Abstracts of Japan, Vol. 16; No. 156 (C-0930), 16.4.1992; EP-A-316179 (Tokuyama Soda KK); GB-A-2058077 (Hudson et al.); and DE-A-2411382 (Boehringer Sohn Ingelheim) describe alkyl ester derivative of 5-aminolevulinic acid, and derivatives and salts thereof and processes for their preparation.

Alternatively viewed, the invention can therefore be seen to provide compounds of formula I, $$R_2^2N\text{—}CH_2COCH_2\text{—}CH_2CO\text{—}OR^1 \qquad (I)$$

(wherein $R^1$ may represent alkyl optionally substituted by hydroxy, alkoxy, acyloxy, alkoxycarbonyloxy, amino, aryl, 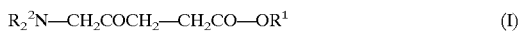

oxo or fluoro groups and optionally interrupted by oxygen, nitrogen, sulphur or phosphorus atoms; and $R^2$, each of which may be the same or different, represents a hydrogen atom or a group $R^1$) and salts thereof for use in photochemotherapy or diagnosis.

The sustituted alkyl $R^1$ groups may be mono or polysubstituted. Thus suitable $R^1$ groups include for example unsubstituted alkyl, alkoxyalkyl, hydroxyalkoxyalkyl, polyhydroxyalkyl, hydroxy poly alkyleneoxyalkyl and the like. The term "acyl" as used herein includes both carboxylate and carbonate groups, thus, acyloxy substituted alkyl groups include for example alkylcarbonyloxy alkyl. In such groups any alkylene moieties preferably have carbon atom contents defined for alkyl groups below. Preferred aryl groups include phenyl and monocyclic 5-7 membered heteroaromatics, especially phenyl and such groups may themselves optionally be substituted.

Representative substituted alkyl groups $R^1$ include alkoxymethyl, alkoxyethyl and alkoxypropyl groups or acyloxymethyl, acyloxyethyl and acyloxypropyl groups eg. pivaloyloxymethyl.

Preferred compounds for use according to the invention, include those wherein $R^1$ represents an unsubstituted alkyl group and/or each $R^2$ represents a hydrogen atom.

As used herein, the term "alkyl" includes any long or short chain, straight-chained or branched aliphatic saturated or unsaturated hydrocarbon group. The unsaturated alkyl groups may be mono- or polyunsaturated and include both alkenyl and alkynyl groups. Such groups may contain up to 40 carbon atoms. However, alkyl groups containing up to 10 eg. 8, more preferably up to 6, and especially preferably up to 4 carbon atoms are preferred.

Particular mention may be made of ALA-methylester, ALA-ethylester, ALA-propylester, ALA-hexylester, ALA-heptylester and ALA-octylester and salts thereof, which represent preferred compounds for use according to the invention.

The compounds for use in the invention may be prepared using standard processes and procedures well-known in the art for derivatization of multi-functional compounds, and especially esterification. As known in the art, such esterification of compounds may involve protection and deprotection of appropriate groups such that only the required groups remain active and take part in the reaction under the conditions of the esterification. Thus for example the substituents of substituted alkanols used to prepare the esters may be protected during esterification. Similarly the $NR_2^2$ group on the compound contributing this group to compounds of formula I may be protected during the reaction and deprotected thereafter. Such protection/deprotection procedures are well known in the art for the preparation of derivatives, and in particular, esters of well known amino-acids, see for example Mcomie in "Protective Groups in Organic Chemistry", Plenum, 1973 and T. W. Greene in "Protective Groups in Organic Chemistry", Wiley-Interscience, 1981.

In a further aspect, the present invention thus provides a process for preparing the compounds for use in the invention, comprising forming an ester of the carboxy group of a 5-aminolevulinic acid.

The invention can thus be seen to provide a process for preparing the compounds for use in the invention, comprising reacting a 5-aminolevulinic acid, or an esterifiable derivative thereof, with an alkanol or an ester-forming derivative thereof.

More particularly, this aspect of the invention provides a process for preparing compounds of formula I, which process comprises at least one of the following steps:

(a) reacting a compound of formula II

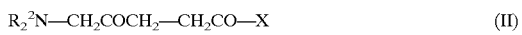

$$R_2^2N\text{—}CH_2COCH_2\text{—}CH_2CO\text{—}X \quad (II)$$

(wherein X represents a leaving group, for example a hydroxyl group, a halogen atom or alkoxy group or COX represents an acid anhydride group and $R^2$ is as hereinbefore defined)

with a compound of formula III

$$R^1\text{—}OH \quad (III)$$

(wherein $R^1$ is as hereinbefore defined); and (b) converting a compound of formula I into a pharmaceutically acceptable salt thereof.

The reaction of step (a) may conveniently be carried out in a solvent or mixture of solvents such as water, acetone, diethylether, methylformamide, tetrahydrofuran etc. at temperatures up to the boiling point of the mixture, preferably at ambient temperatures. The conditions of the esterification reactions will depend on the alcohol used and the conditions may be chosen such that maximum yield of the ester is obtained. Since the esterification reactions are reversible equilibrium reactions, reaction conditions may be selected in such a way that maximum yield of the ester product is obtained. Such conditions may be obtained by selecting a solvent which is capable of removing the water formed in a typical esterification reaction by forming an azeotrope with water. Such solvents are exemplified by aromatic hydrocarbons or others capable of forming azeotropes with water, e.g. some chlorinated hydrocarbons such as chloroform. For the formation of the lower esters of 5-ALA the equilibrium reaction may be driven to the ester side by using a large excess of the alcohol. With other esters the equilibrium may be driven towards the ester product by using a large excess of the acid.

Esterification reactions are well-known in the art for example, as described by Saul Patai in "The chemistry of the carboxylic acids and esters", (Ch. 11, p. 505, Interscience 1969) and Houban Weyl, (Methoden der Organische Chemie, Band ES, "Carbonsauren und carbonsauren-derivate", p. 504, Georg Thieme Verlag, 1985). The formation of derivatives of amino-acids are described in Band XI/2 of the same series, (Houben Weyl, Methoden der Organische Chemie, Band XI/2, "Stickstoffverbindungen", p. 269, Georg Thieme Verlag, 1958).

The reaction will conveniently be carried out in the presence of a catalyst, eg. an inorganic or organic acid or an acid binding agent such as a base.

The compounds used as starting materials are known from the literature, and in many cases commercially available, or may be obtained using methods known per se. ALA, for example, is available from Sigma or from Photocure, Oslo, Norway.

As mentioned above, the compounds for use according to the invention may take the form of pharmaceutically acceptable salts. Such salts preferably are acid addition salts with physiologically acceptable organic or inorganic acids. Suitable acids include, for example, hydrochloric, hydrobromic, sulphuric, phosphoric, acetic, lactic, citric, tartaric, succinic, maleic, fumaric and ascorbic acids. Procedures for salt formation are conventional in the art.

As mentioned above, the compounds for use according to the invention and their salts have valuable pharmacological properties, namely a photosensitizing agent which renders them useful as photochemotherapeutic agents.

Like ALA, the compounds exert their effects by enhancing production of Pp; upon delivery to the desired site of action hydrolytic enzymes such as esterases present in the target cells break down the esters into the parent ALA, which then enters the haem synthesis pathway and leads to a build-up of Pp. However, the compounds for use according to the invention have a number of advantages over ALA itself. Firstly, the novel compounds are better able to penetrate skin and other tissues as compared with ALA; the penetration is both deeper and faster. This is an important advantage, especially for topical administration. Secondly, the esters have surprisingly been found to be better enhancers of Pp production than ALA; Pp production levels following administration of the ALA esters are higher than with ALA alone. Thirdly, the compounds for use in the invention demonstrate improved selectivity for the target tissue to be treated, namely the Pp production-enhancing effect is localised to the desired target lesion and does not spread to the surrounding tissues. This is especially evident with tumours. Finally, the compounds appear to localise better to the target tissue upon administration. This is especially important for systemic application, since it means that undesirable photosensitization effects, as reported in the literature for other porphyrin-based photosensitizers, may be reduced or avoided.

A further aspect of the present invention accordingly provides a pharmaceutical composition comprising a compound as described hereinbefore, or a pharmaceutically acceptable salt thereof, together with at least one pharmaceutical carrier or excipient.

In a still further aspect, there is also provided the use of a compound as described hereinbefore, or a pharmaceutically acceptable salt thereof, for the preparation of a therapeutic agent for use in photochemotherapy, and especially for the treatment of disorders or abnormalities of external or internal surfaces of the body which are responsive to photochemotherapy.

The abnormalities and disorders which may be treated according to the present invention include any malignant, pre-malignant and non-malignant abnormalities or disorders responsive to photochemotherapy eg. tumours or other growths, skin disorders such as psoriasis or actinic keratoses, skin abrasions, and other diseases or infections eg. bacterial, viral or fungal infections, for example Herpes virus infections. The invention is particularly suited to the treatment of diseases, disorders or abnormalities where discrete lesions are formed to which the compositions may be directly applied (lesions is used here in a broad sense to include tumours and the like).

The internal and external body surfaces which may be treated according to the invention include the skin and all other epithelial and serosal surfaces, including for example mucosa, the linings of organs eg. the respiratory, gastrointestinal and genito-urinary tracts, and glands with ducts which empty onto such surfaces (e.g. liver, hair follicles with sebaceous glands, mammary glands, salivary glands and seminal vesicles). In addition to the skin, such surfaces include for example the lining of the vagina, the endometrium and the urothelium. Such surfaces may also include cavities formed in the body following excision of diseased or cancerous tissue eg. brain cavities following the excision of tumours such as gliomas.

Exemplary surfaces thus include: (i) skin and conjunctiva; (ii) the lining of the mouth, pharynx, oesophagus, stomach, intestines and intestinal appendages, rectum, and anal canal; (iii) the lining of the nasal passages, nasal sinuses, nasopharynx, trachea, bronchi, and bronchioles; (iv) the lining of the ureters, urinary bladder, and urethra; (v) the lining of the vagina, uterine cervix, and uterus; (vi) the parietal and visceral pleura; (vii) the lining of the peritoneal and pelvic cavities, and the surface of the organs contained within those cavities; (viii) the dura mater and meninges; (ix) any tumors in solid tissues that can be made accessible to photoactivating light e.g. either directly, at time of surgery, or via an optical fibre inserted through a needle.

The compositions of the invention may be formulated in conventional manner with one or more physiologically acceptable carriers or excipients, according to techniques well known in the art. Compositions may be administered topically, orally or systemically. Topical compositions are preferred, and include gels, creams, ointments, sprays, lotions, salves, sticks, soaps, powders, pessaries, aerosols, drops and any of the other conventional pharmaceutical forms in the art.

Ointments and creams may, for example, be formulated with an aqueous or oily base with the addition of suitable thickening and/or gelling agents. Lotions may be formulated with an aqueous or oily base and will, in general, also contain one or more emulsifying, dispersing, suspending, thickening or colouring agents. Powders may be formed with the aid of any suitable powder base. Drops may be formulated with an aqueous or non-aqueous base also comprising one or more dispersing, solubilising or suspending agents. Aerosol sprays are conveniently delivered from pressurised packs, with the use of a suitable propellant.

Alternatively, the compositions may be provided in a form adapted for oral or parenteral administration, for example by intradermal, subcutaneous, intraperitoneal or intravenous injection. Alternative pharmaceutical forms thus include plain or coated tablets, capsules, suspensions and solutions containing the active component optionally together with one or more inert conventional carriers and/or diluents, e.g. with corn starch, lactose, sucrose, microcrystalline cellulose, magnesium stearate, polyvinylpyrrolidone, citric acid, tartaric acid, water, water/ethanol, water/glycerol, water/sorbitol, water/polyethyleneglycol, propyleneglycol, stearylalcohol, carboxymethylcellulose or fatty substances such as hard fat or suitable mixtures thereof.

The concentration of the compounds as described hereinbefore the invention in the compositions, depends upon the nature of the compound, the composition, mode of administration and the patient and may be varied or adjusted according to choice. Generally however, concentration ranges of 1 to 50% (w/w) are suitable. For therapeutic applications concentration ranges of 10 to 50% have been found to be suitable, eg. 15 to 30% (w/w).

Following administration to the surface, the area treated is exposed to light to achieve the photochemotherapeutic effect. The length of time following administration, at which the light exposure takes place will depend on the nature of the composition and the form of administration. This can generally be in the order of 0.5 to 48 hours, e.g. 1 to 10 hours.

The irradiation will in general be applied at a dose level of 40 to 200 Joules/cm$^2$, for example at 100 Joules/cm$^2$.

The wavelength of light used for irradiation may be selected to achieve a more efficaceous photochemotherapeutic effect. Conventionally, when porphyrins are used in photochemotherapy they are irradiated with light at about the absorption maximum of the porphyrin. Thus, for example in the case of the prior art use of ALA in photochemotherapy of skin-cancer, wavelengths in the region 350–640 nm, preferably 610–635 nm were employed. However, by selecting a broad range of wavelengths for irradiation, extending beyond the absorption maximum of the porphyrin, the photosensitizing effect may be enhanced.

Whilst not wishing to be bound by theory, this is thought to be due to the fact that when Pp, and other porphyrins, are exposed to light having wavelengths within its absorption spectrum, it is degraded into various photo-products including in particular photoprotoporphyrin (PPp). PPp is a chlorin and has a considerable photo-sensitizing effect; its absorption spectrum stretches out to longer wavelengths beyond the wavelengths at which Pp absorbs ie. up to almost 700 nm (Pp absorbs almost no light above 650 nm). Thus in conventional photochemotherapy, the wavelengths used do not excite PPp and hence do not obtain the benefit of its additional photosensitizing effect. Irradiation with wavelengths of light in the range 500–700 nm has been found to be particularly effective. It is particularly important to include the wavelengths 630 and 690 nm.

A further aspect of the invention thus provides a method of photochemotherapeutic treatment of disorders or abnormalities of external or internal surfaces of the body, comprising administering to the affected surfaces, a composition as hereinbefore defined, and exposing said surfaces to light, preferably to light in the wavelength region 300–800 nm, for example 500–700 nm.

Methods for irradiation of different areas of the body, eg. by lamps or lasers are well known in the art (see for example Van den Bergh, Chemistry in Britain, May 1986 p. 430–439).

The compounds for use in the invention may be formulated and/or administered with other photosensitizing agents, for example ALA or photofrin, or with other active components which may enhance the photochemotherapeutic effect. For example, chelating agents may beneficially be included in order to enhance accumulation of Pp; the chelation of iron by the chelating agents prevents its incorporation into Pp to form haem by the action of the enzyme ferrochelatase, thereby leading to a build-up of Pp. The photosensitizing effect is thus enhanced. Aminopolycarboxylic acid chelating agents are particularly suitable for use in this regard, including any of the chelants described in the literature for metal detoxification or for the chelation of paramagnetic metal ions in magnetic resonance imaging contrast agents. Particular mention may be made of EDTA, CDTA (cyclohexane diamine tetraacetic acid), DTPA and DOTA. EDTA is preferred. To achieve the ironchelating effect, desferrioxamine and other siderophores may also be used, e.g. in conjunction with aminopolycarboxylic acid chelating agents such as EDTA.

The chelating agent may conveniently be used at a concentration of 1 to 20% eg. 2 to 10% (w/w).

Additionally, it has been found that surfacepenetration assisting agents and especially dialkylsuphoxides such as dimethylsulphoxide (DMSO) may have a beneficial effect in enhancing the photochemotherapeutic effect. This is described in detail in our co-pending application No. PCT/GB94/01951, a copy of the specification of which is appended hereto.

The surface-penetration assisting agent may be any of the skin-penetration assisting agents described in the pharmaceutical literature e.g. HPE-101 (available from Hisamitsu), DMSO and other dialkylsulphoxides, in particular n-decylmethyl-sulphoxide (NDMS), dimethylsulphacetamide, dimethylformamide (DMFA), dimethylacetamide, glycols, various pyrrolidone derivatives (Woodford et al., J. Toxicol. Cut. & Ocular Toxicology, 1986, 5: 167–177), and Azone® (Stoughton et al., Drug Dpv. Ind. Pharm. 1983, 9: 725–744), or mixtures thereof.

DMSO however has a number of beneficial effects and is strongly preferred. Thus, in addition to the surface-penetration assisting effect (DMSO is particularly effective in enhancing the depth of penetration of the active agent into the tissue), DMSO has anti-histamine and anti-inflammatory activities. In addition, DMSO has been found to increase the activity of the enzymes ALA-synthase and ALA-dehydrogenase (the enzymes which, respectively, form and condense ALA to porphobilinogen) thereby enhancing the formation of the active form, Pp.

The surface penetration agent may conveniently be provided in a concentration range of 2 to 50% (w/w), eg about 10% (w/w).

According to the condition being treated, and the nature of the composition, the compounds for use in the invention may be co-administered with such other optional agents, for example in a single composition or they may be administered sequentially or separately. Indeed, in many cases a particularly beneficial photochemotherapeutic effect may be obtained by pretreatment with the surface-penetration assisting agent in a separate step, prior to administration of the compounds for use in the invention. Furthermore, in some situations a pre-treatment with the surface-penetration assisting agent, followed by administration of the photochemotherapeutic agent in conjunction with the surface-penetration assisting agent may be beneficial. When a surface-penetration assisting agent is used in pre-treatment this may be used at high concentrations, e.g. up to 100% (w/w). If such a pre-treatment step is employed, the photochemotherapeutic agent may subsequently be administered up to several hours following pre-treatment eg. at an interval of 5–60 minutes following pre-treatment.

Viewed from a further aspect, the invention thus provides a product comprising a compound as described hereinbefore or a pharmaceutically acceptable salt thereof, together with at least one surface-penetration assisting agent, and optionally one or more chelating agents as a combined preparation for simultaneous, separate or sequential use in treating disorders or abnormalities of external or internal surfaces of the body which are responsive to photochemotherapy.

Alternatively viewed, this aspect of the invention also provides a kit for use in photochemotherapy of disorders or abnormalities of external or internal surfaces of the body comprising:

a) a first container containing a compound as described hereinbefore invention or a pharmaceutically acceptable salt thereof, b) a second container containing at least one surface penetration assisting agent; and optionally c) one or more chelating agents contained either within said first container or in a third container.

Where the surface penetration agent is applied in a separate pre-treatment step, it may be applied in higher concentration, for example up to 100% (w/w).

It will be appreciated that the method of therapy using compounds of the invention inevitably involves the fluorescence of the disorder or abnormality to be treated. Whilst the intensity of this fluorescence may be used to eliminate abnormal cells, the localization of the fluorescence may be used to visualize the size, extent and situation of the abnormality or disorder. This is made possible through the surprising ability of ALA esters to preferentially localize to non-normal tissue.

The abnormality or disorder thus identified or confirmed at the site of investigation may then be treated through alternative therapeutic techniques e.g. surgical or chemical treatment, or by the method of therapy of the invention by continued build up of fluorescence or through further application of compounds of the invention at the appropriate site.

It will be appreciated that diagnostic techniques may require lower levels of fluorescence for visualization than used in therapeutic treatments. Thus, generally, concentration ranges of 1 to 50% e.g. 1–5% (w/w) are suitable. Sites, methods and modes of administration have been considered before with regard to the therapeutic uses and are applicable also to diagnostic uses described here. The compounds for use in the invention may also be used for in vitro diagnostic techniques, for example for examination of the cells contained in body fluids. The higher fluoresence associated with non-normal tissue may conveniently be indicative of an abnormality or disorder. This method is highly sensitive and may be used for early detection of abnormalities or disorders, for example bladder or lung carcinoma by examination of the epithelial cells in urine or sputum samples, respectively. Other useful body fluids which may be used for diagnosis in addition to urine and sputum include blood, semen, tears, spinal fluid etc. Tissue samples or preparations may also be evaluated, for example biopsy tissue or bone marrow samples. The present invention thus extends to the use of compounds of the invention, or salts thereof for diagnosis according to the aforementioned methods for photochemotherapy, and products and kits for performing said diagnosis.

A further aspect of the invention relates to a method of in vitro diagnosis, of abnormalities or disorders by assaying a sample of body fluid or tissue of a patient, said method comprising at least the following steps:

i) admixing said body fluid or tissue with a compound as described hereinbefore, ii) exposing said mixture to light, iii) ascertaining the level of fluorescence, and iv) comparing the level of fluorescence to control levels.

The invention will now be described in more detail in the following non-limiting Examples, with reference to the drawings in which.

Figure 3:
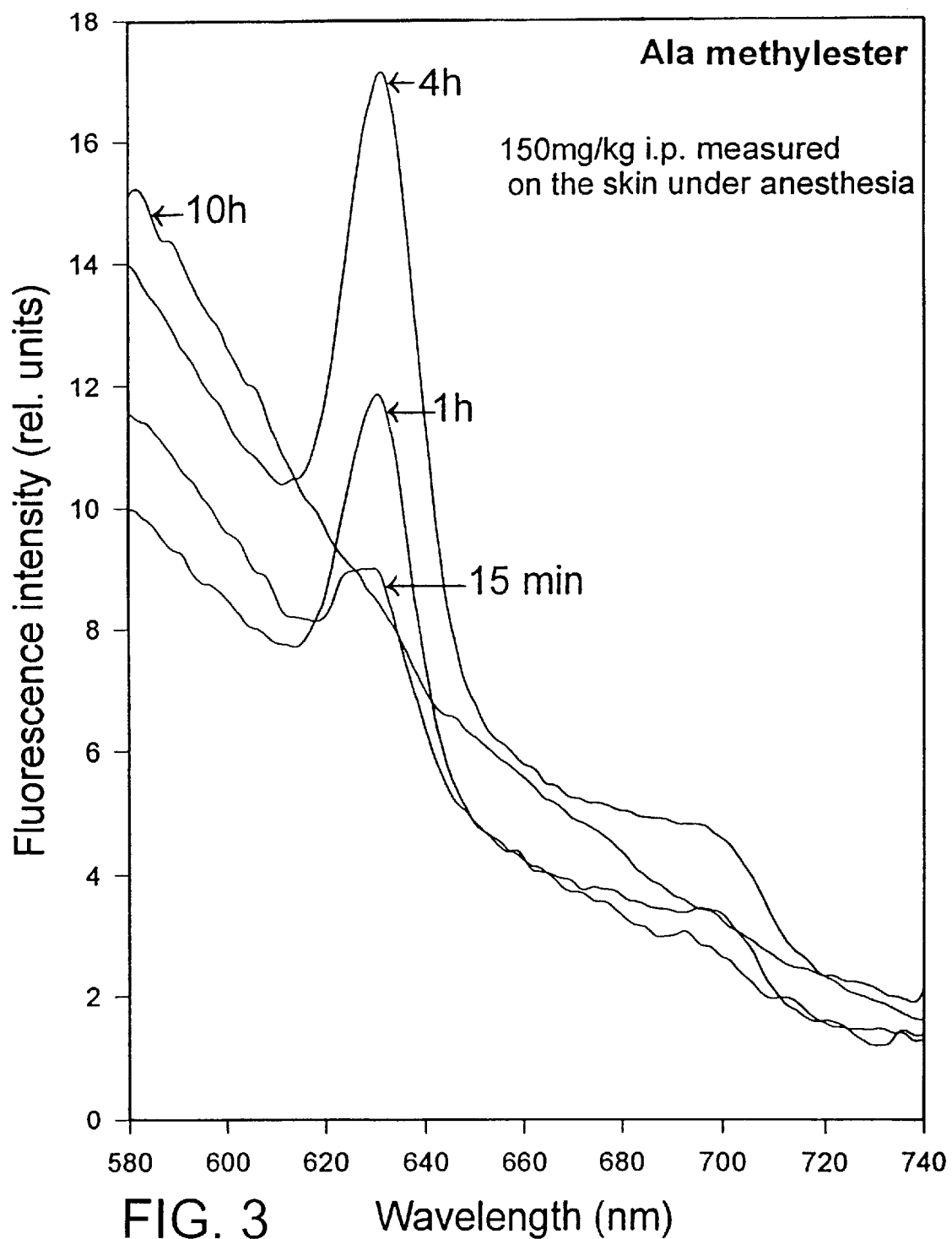
Figure 4:
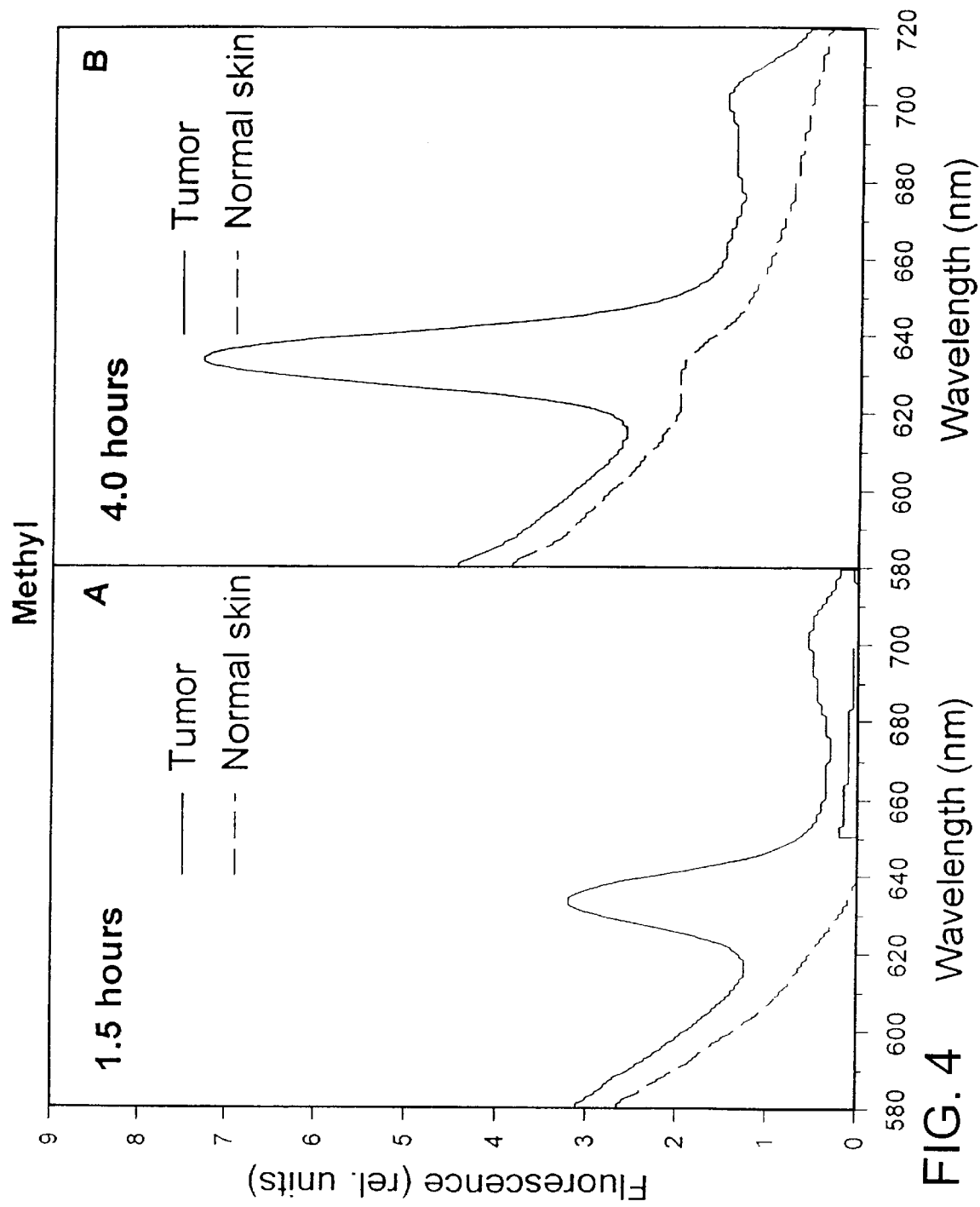
Figure 5:
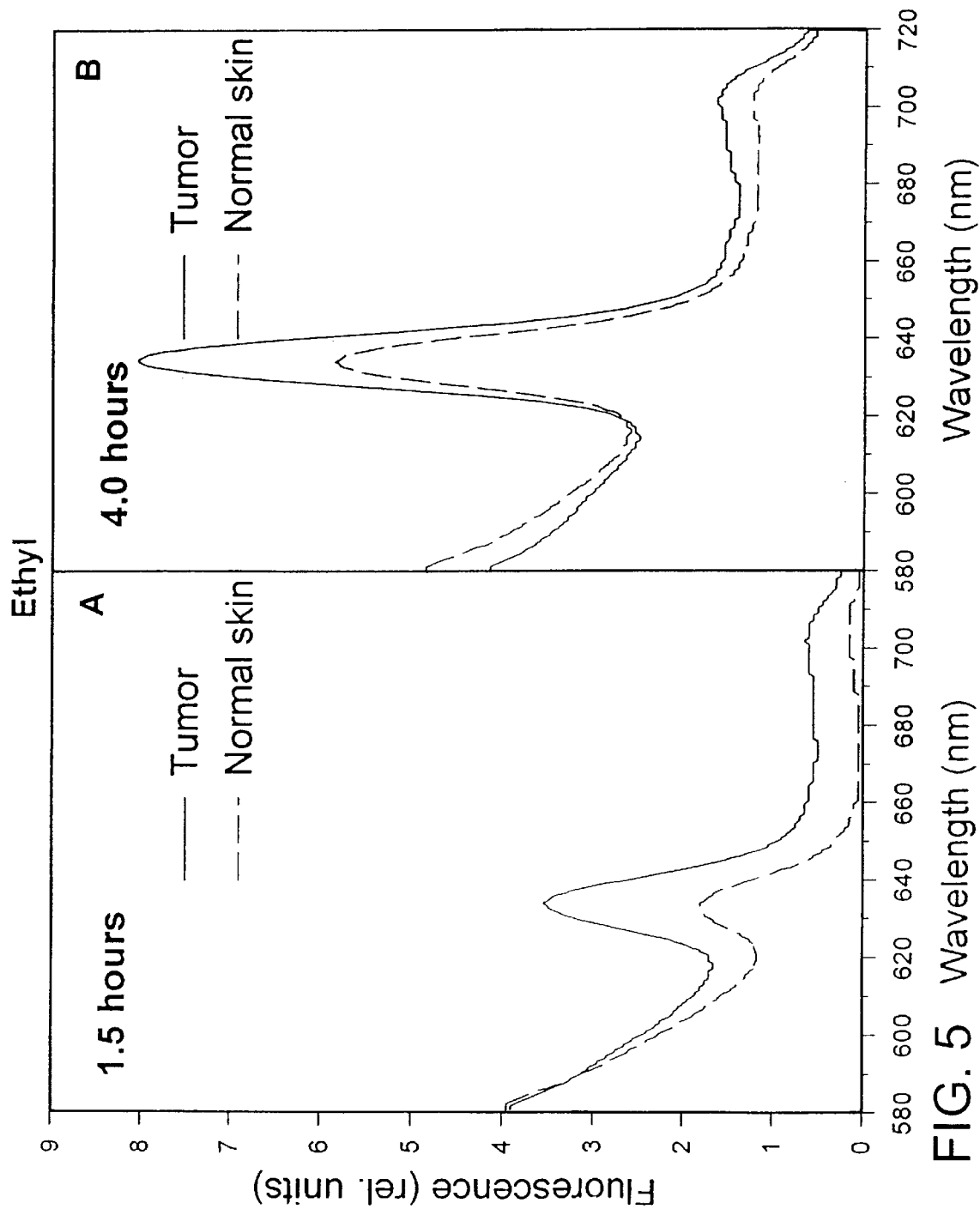
Figure 6:
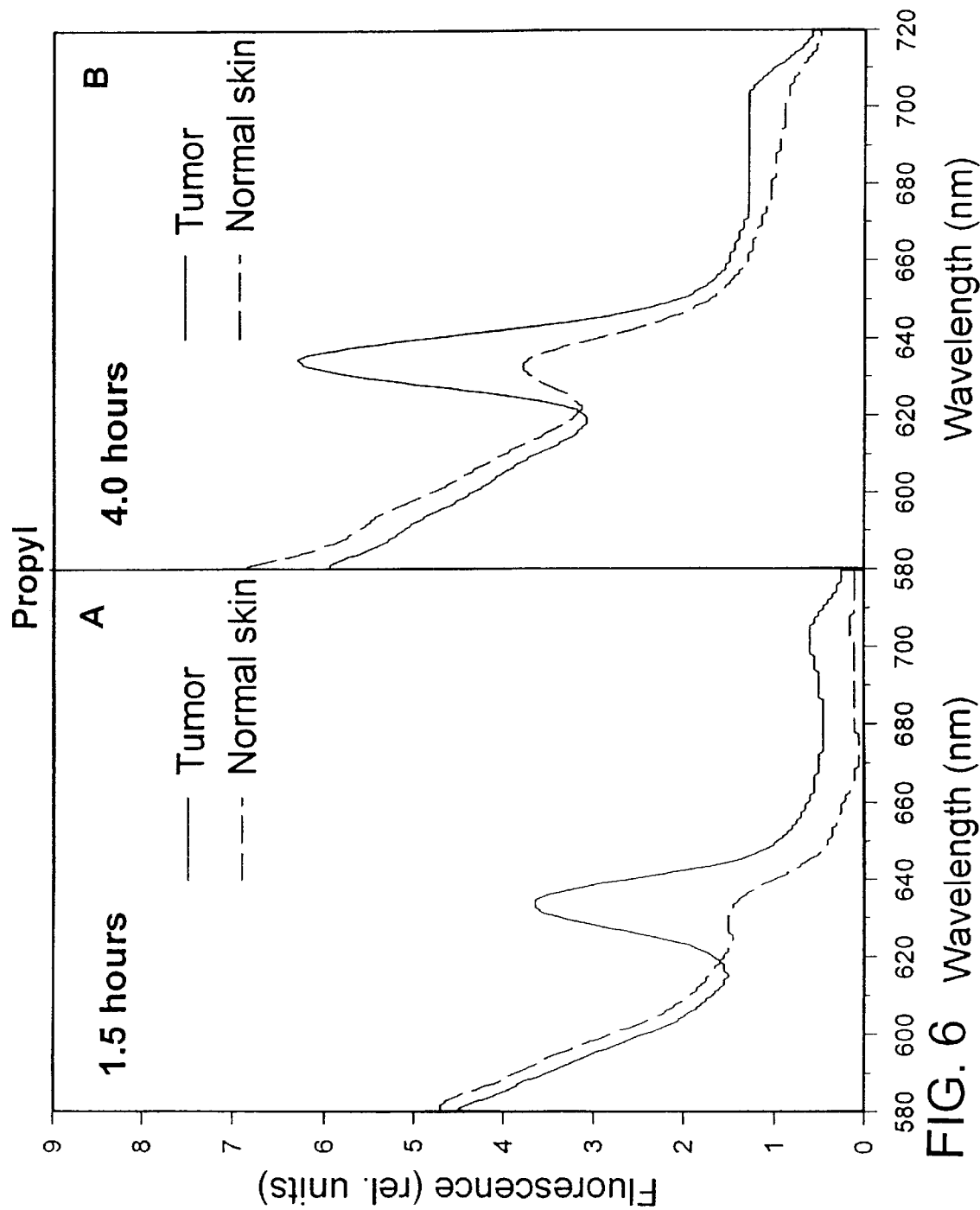
Figure 7:
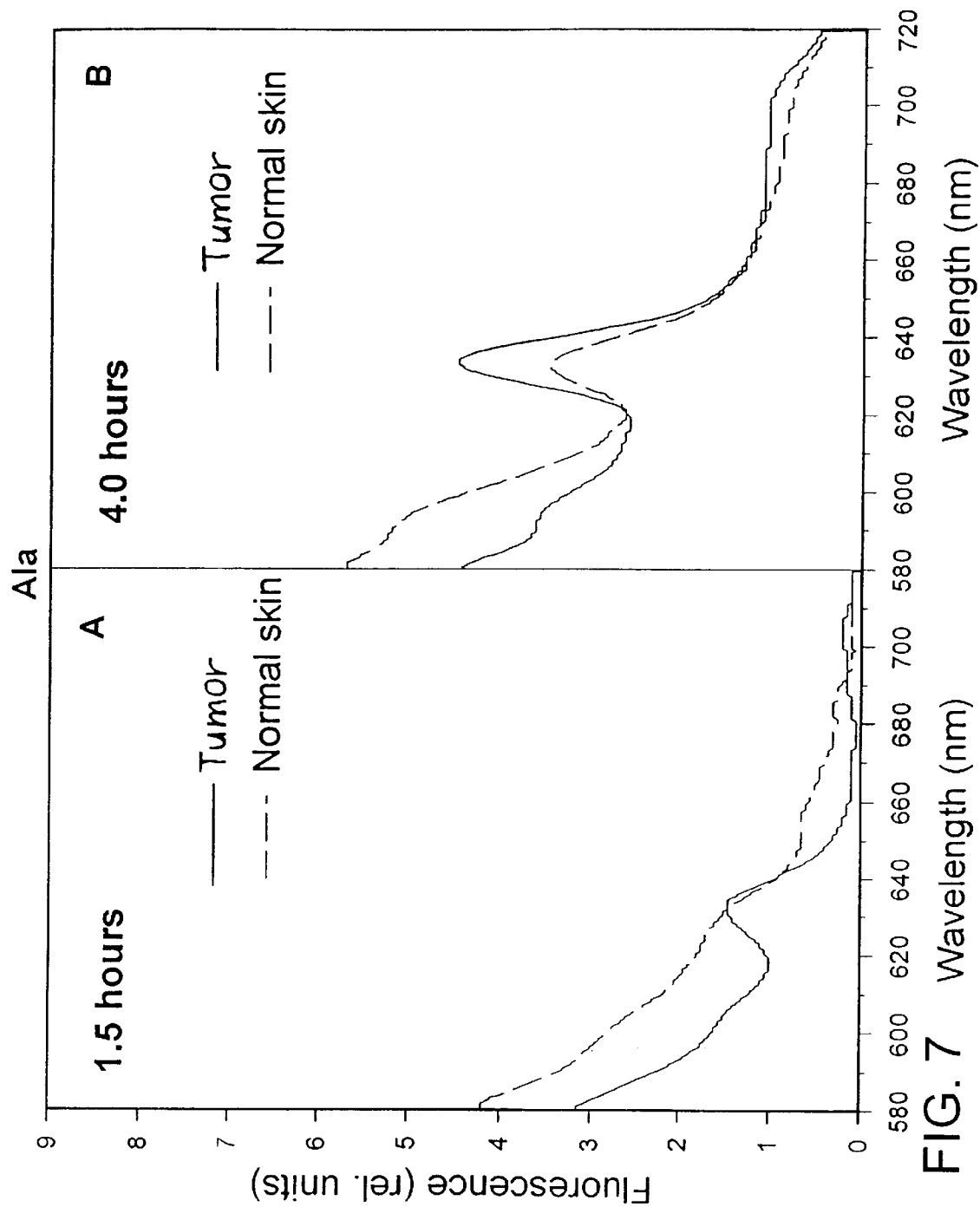
Figure 8:
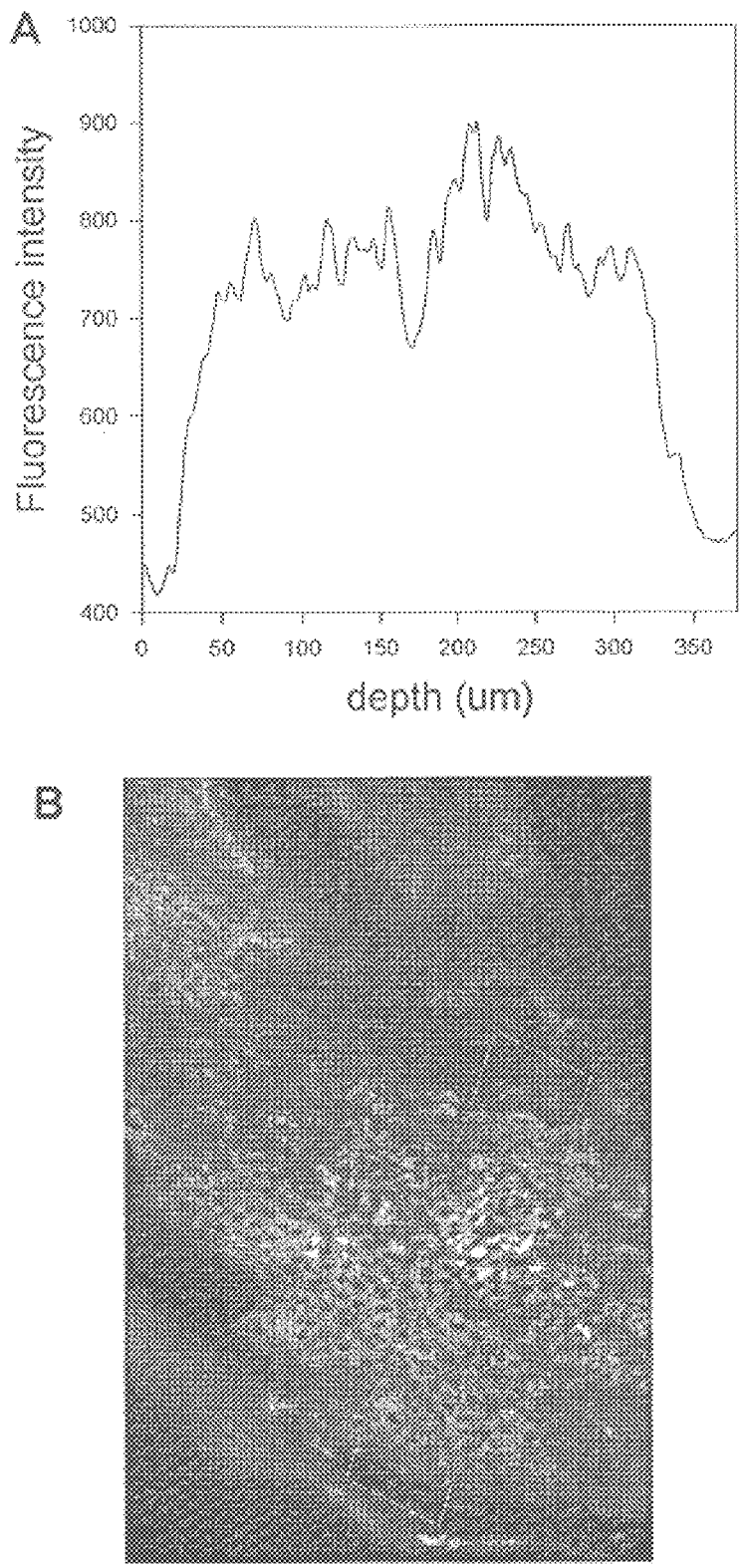
Figure 9:
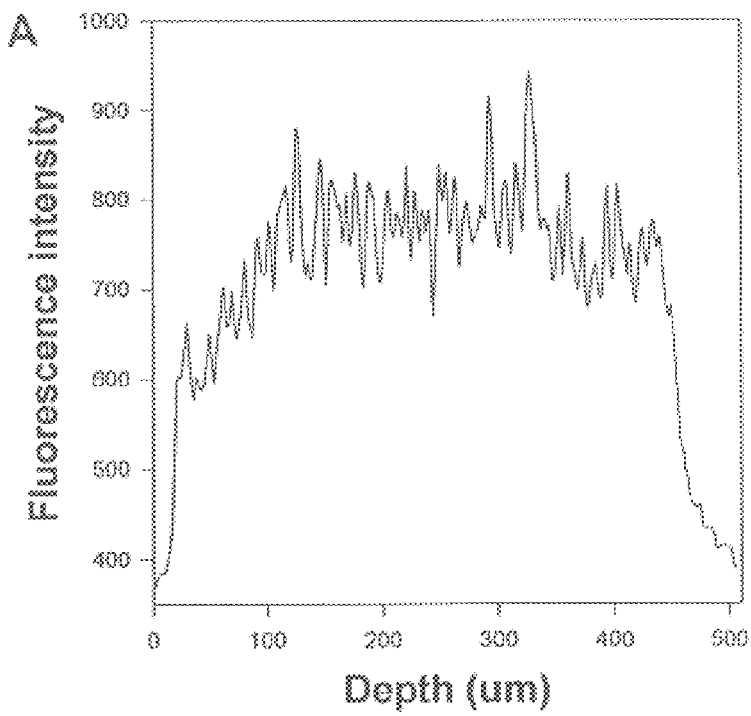
Figure 9:
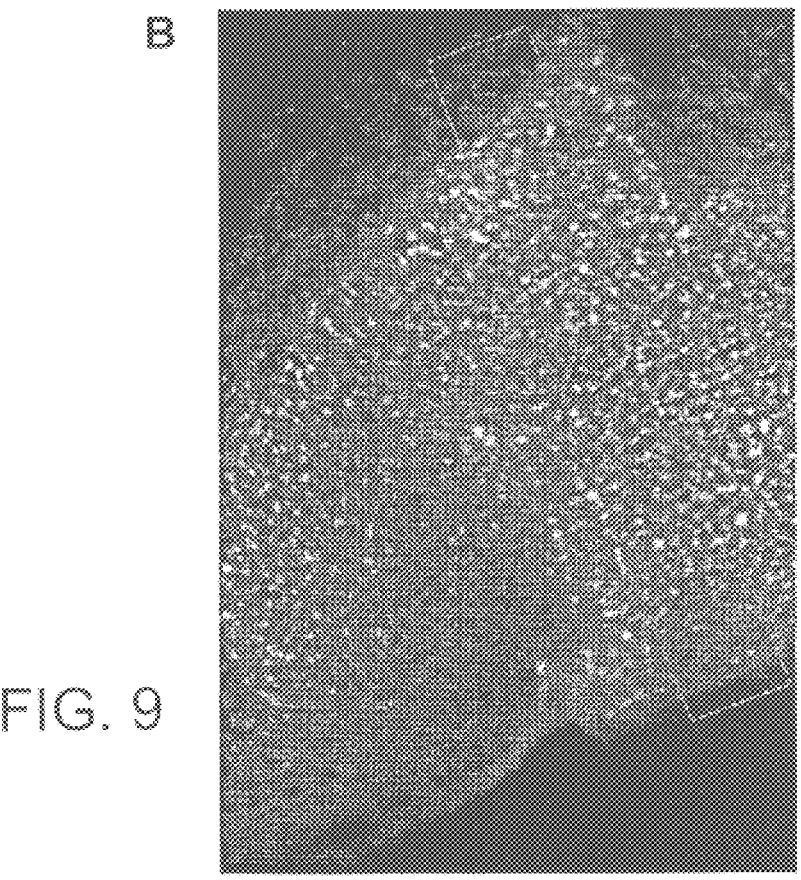
Figure 10:
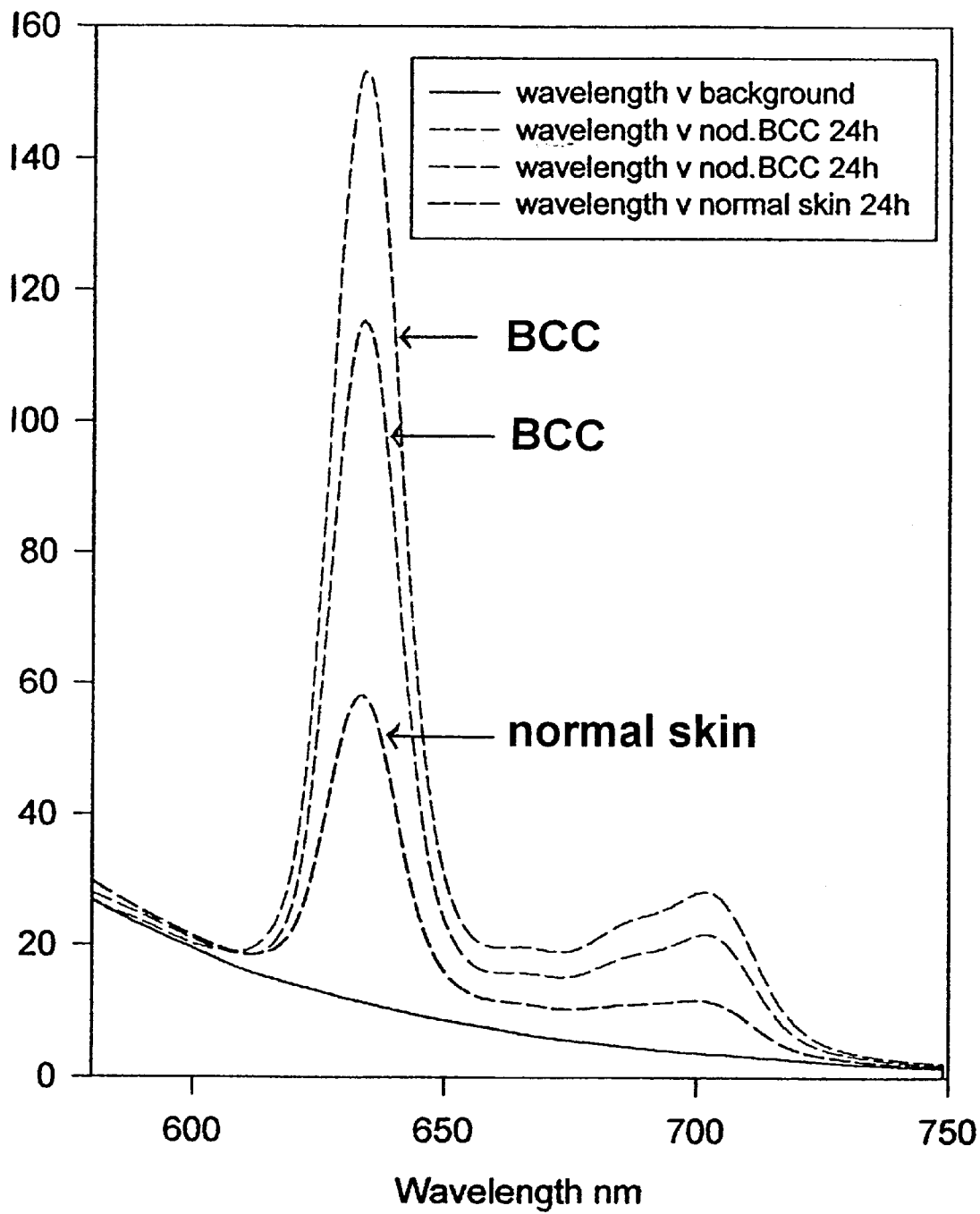

(A) free ALA
(B) ALA methylester
(C) ALA ethylester
(D) ALA propylester;

FIG. 3 shows PPIX fluorescence (fluorescence intesity, relative units vs wavelength (nm)) in the skin of mice 15 minutes, 1 hour, 4 hours and 10 hours after intraperitoneal injection of ALA methylester (150 mg/kg);

FIG. 4 shows PpIX fluorescence (fluorescence intensity relative units vs wavelength (nm)) (A) 1.5 hours and (B) 4 hours after topical administration of ALA methylester to basal cell carcinoma (BCC) lesions on the skin of human patients (–tumour; - - - normal skin);

FIG. 5 shows PpIX fluorescence (fluorescence intensity relative units vs wavelength (nm)) (A) 1.5 hours and (B) 4 hours after topical administration of ALA ethylester to basal cell carcinoma (BCC) lesions on the skin of human patients (–tumour; - - - normal skin);

FIG. 6 shows PpIX fluorescence (fluorescence intensity relative units vs wavelength (nm)) (A) 1.5 hours and (B) 4 hours after topical administration of ALA propylester to basal cell carcinoma (BCC) lesions on the skin of human patients (–tumour; - - - normal skin);

FIG. 7 shows PpIX fluorescence (fluorescence intensity relative units vs wavelength (nm)) (A) 1.5 hours and (B) 4 hours after topical administration of ALA to basal cell carinoma (BCC) lesions on the skin of human patients (–tumour; - - - normal skin);

FIG. 8 shows measurement of PpIX production following topical application of ALA methylester in human BCC and surrounding normal skin by CDD microscopy of biopsies (A) graphical representation showing fluorescence intensity vs depth ($\mu$m) and (B) micrograph;

FIG. 9 shows measurement of PpIX production following topical application of ALA in human BCC and surrounding normal skin by CDD microscopy of biopsies (A) graphical representation showing fluorescence intensity vs depth ($\mu$m) and (B) micrograph;

FIG. 10 shows PPIX fluorescence (fluorescence intensity relative units vs wavelength (nm)) 24 hours following topical administration of ALA methylester to BCC lesion and to normal skin of human patients.

Figure 11:
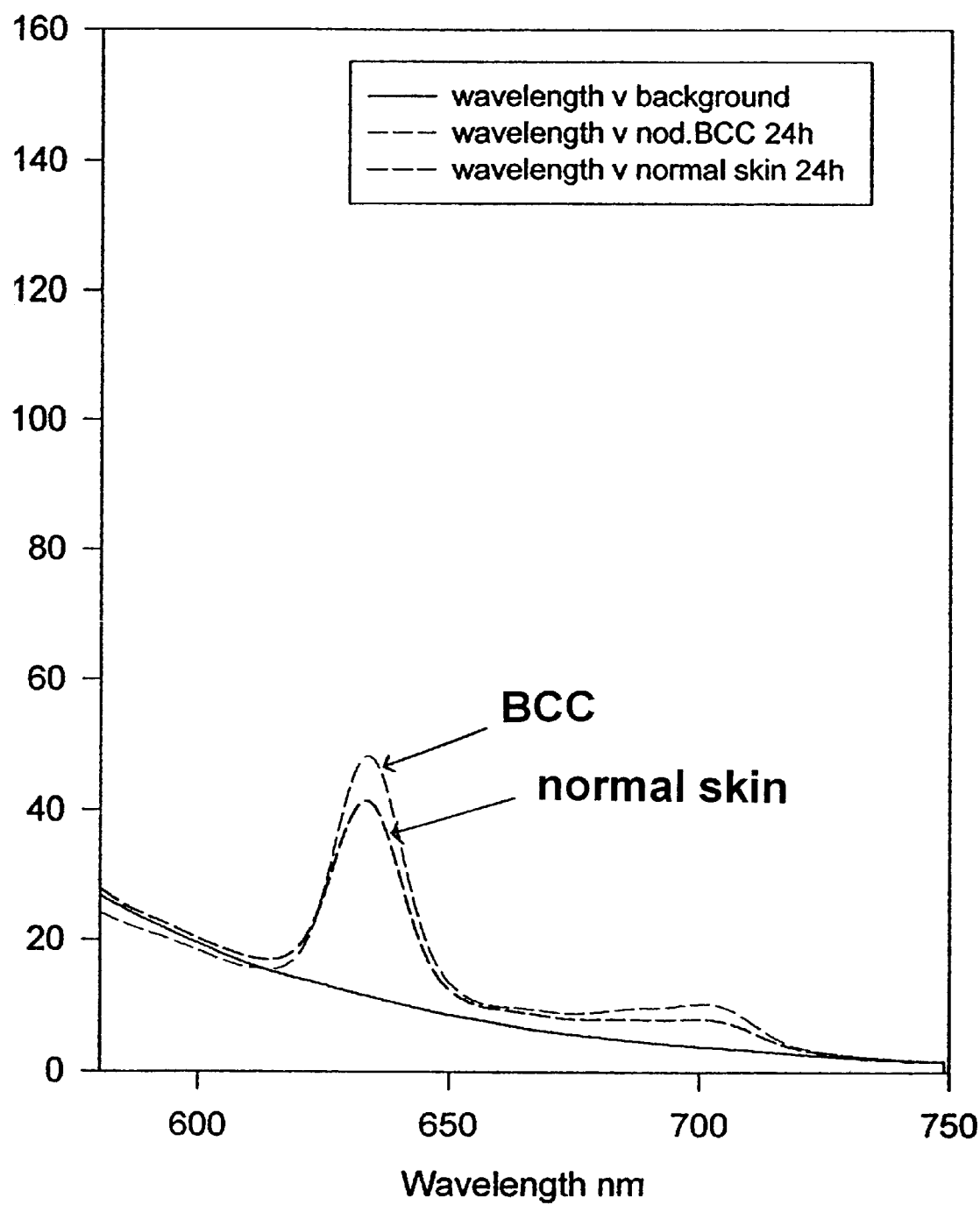

FIG. 11 shows PpIX fluorescence (fluorescence intensity relative units vs wavelength (nm)) 24 hours following topical administration of ALA to BCC lesion and to normal skin of human patients.

Figure 12:
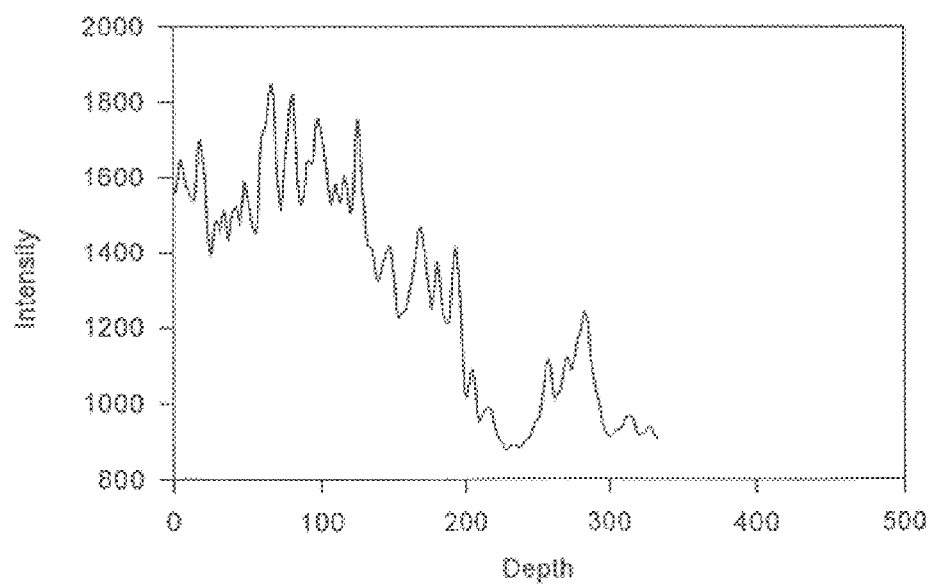
Figure 12:
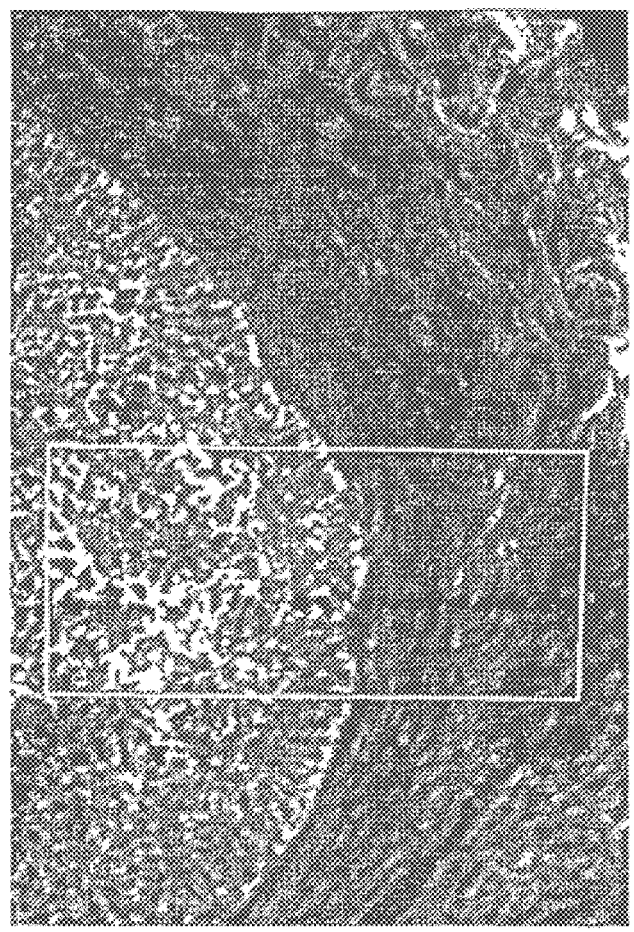
Figure 13:
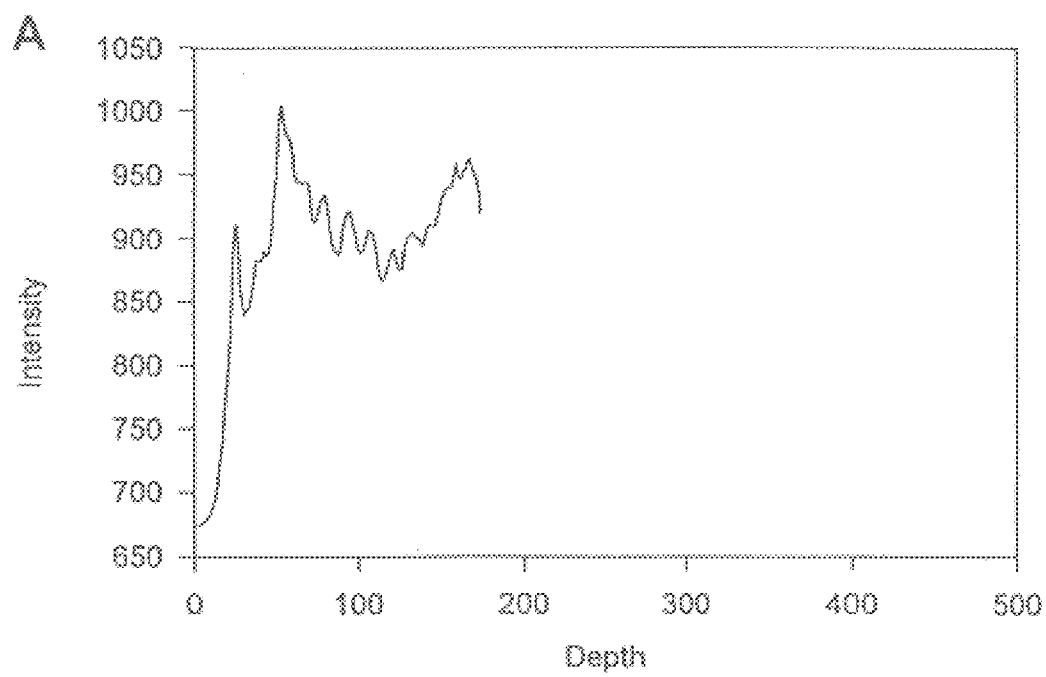
Figure 13:
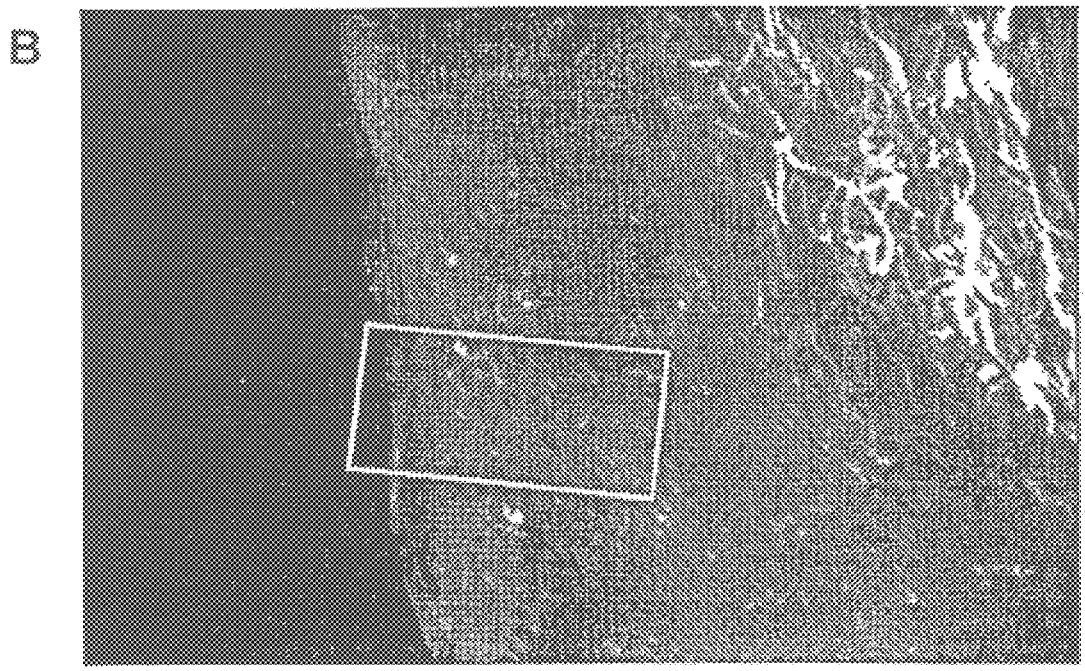
Figure 14:
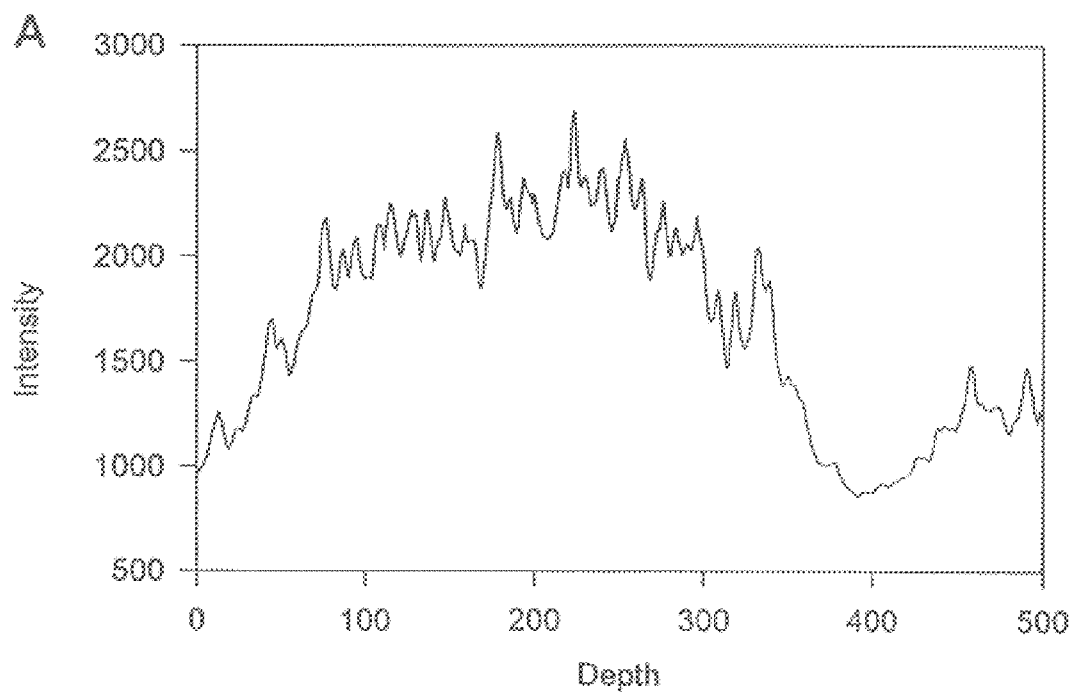
Figure 14:
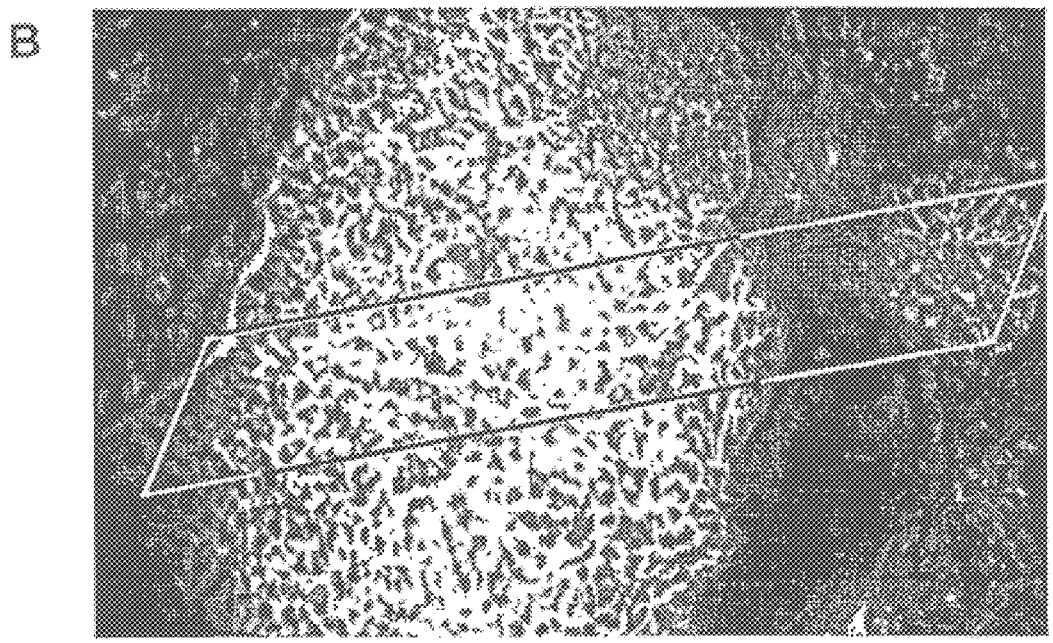
Figure 15:
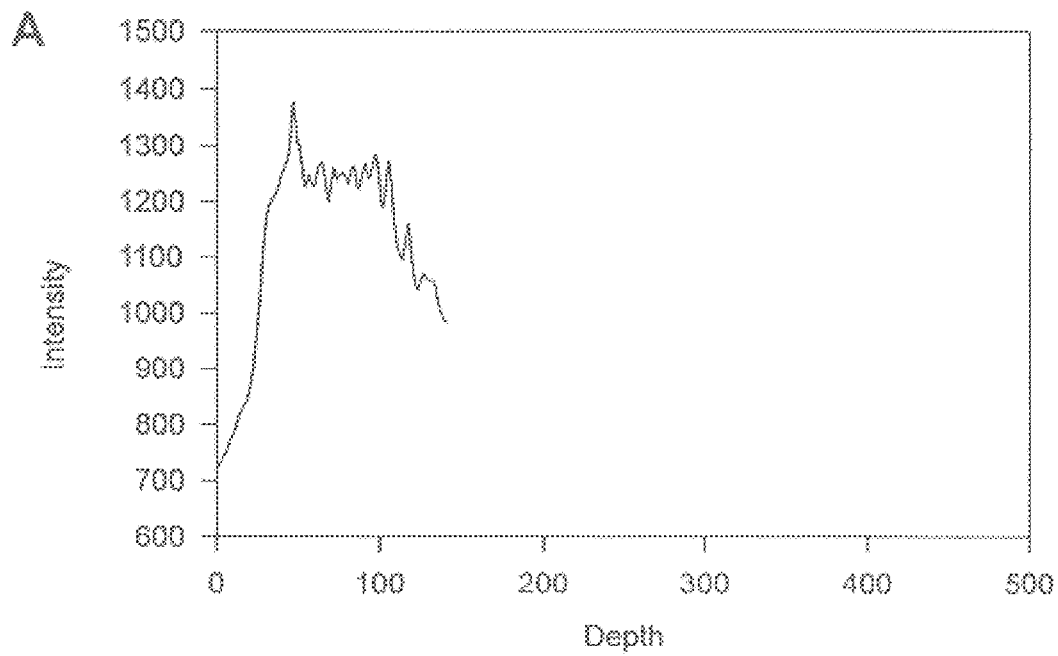
Figure 15:
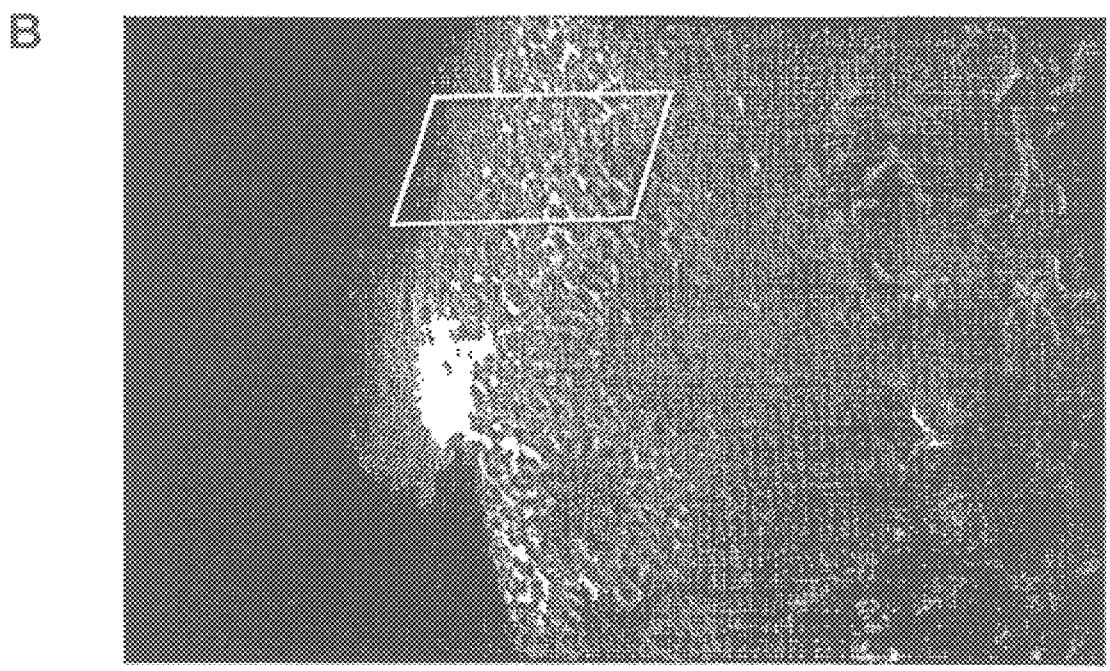
Figure 16:
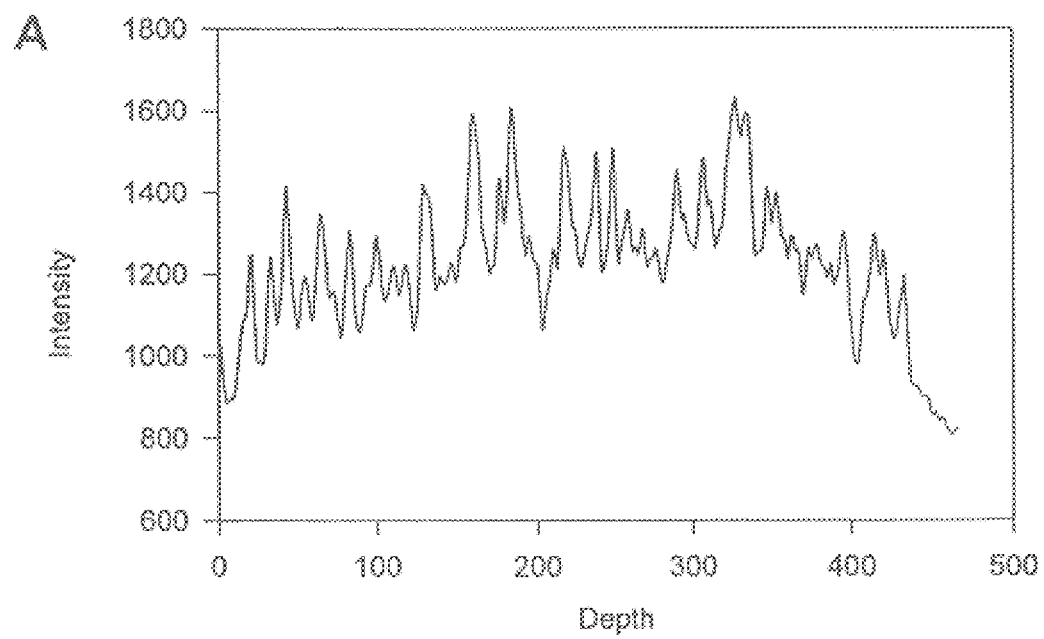
Figure 16:
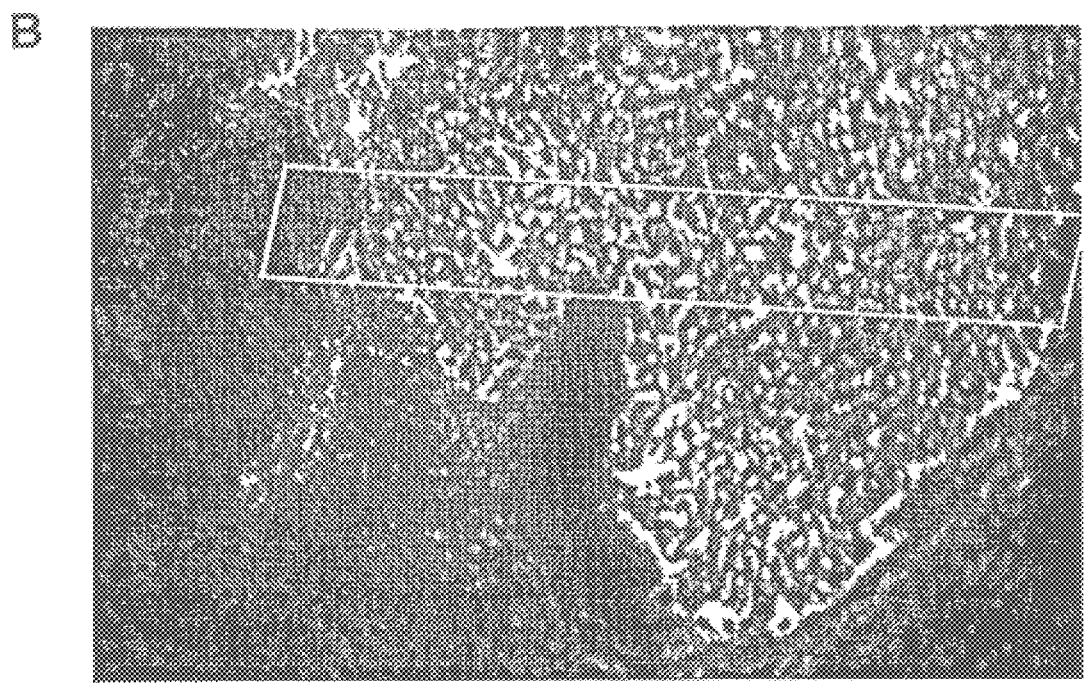
Figure 17:
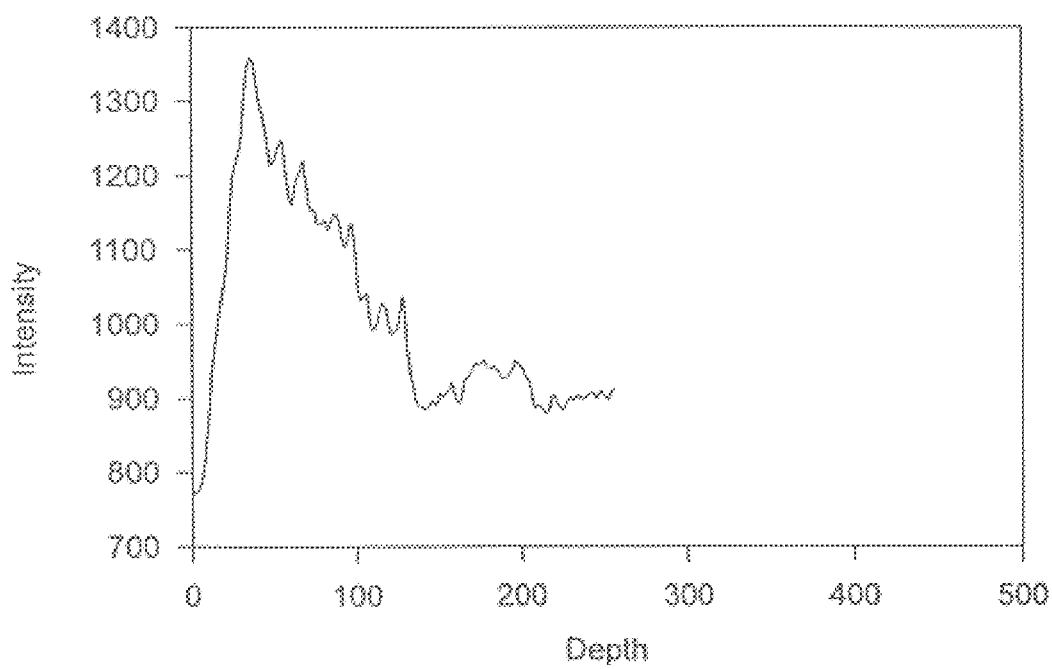
Figure 17:
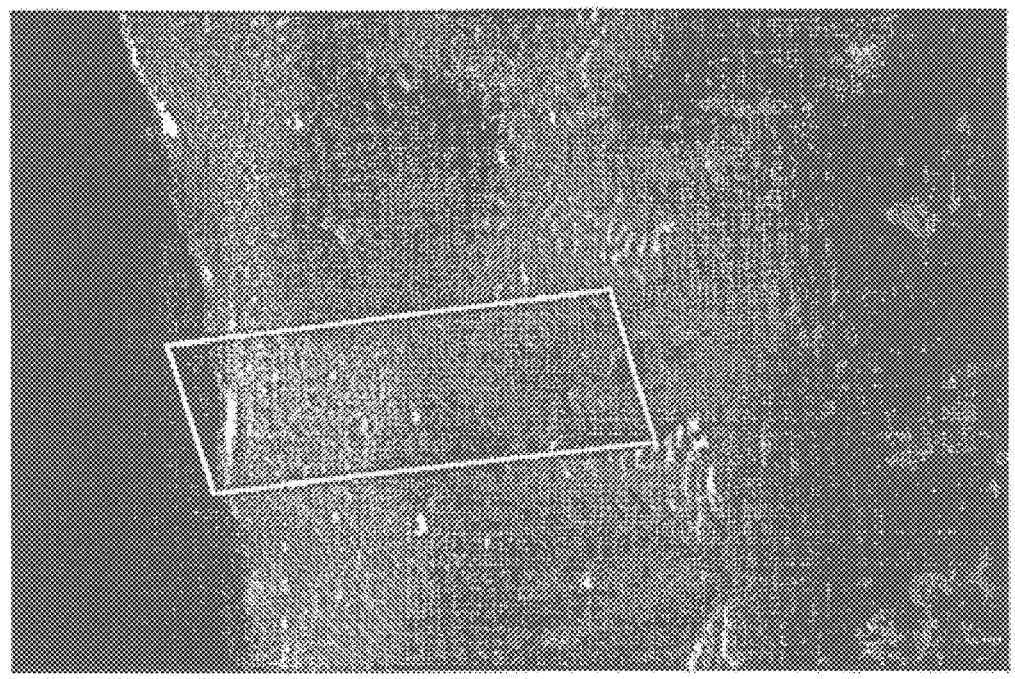
Figure 18:
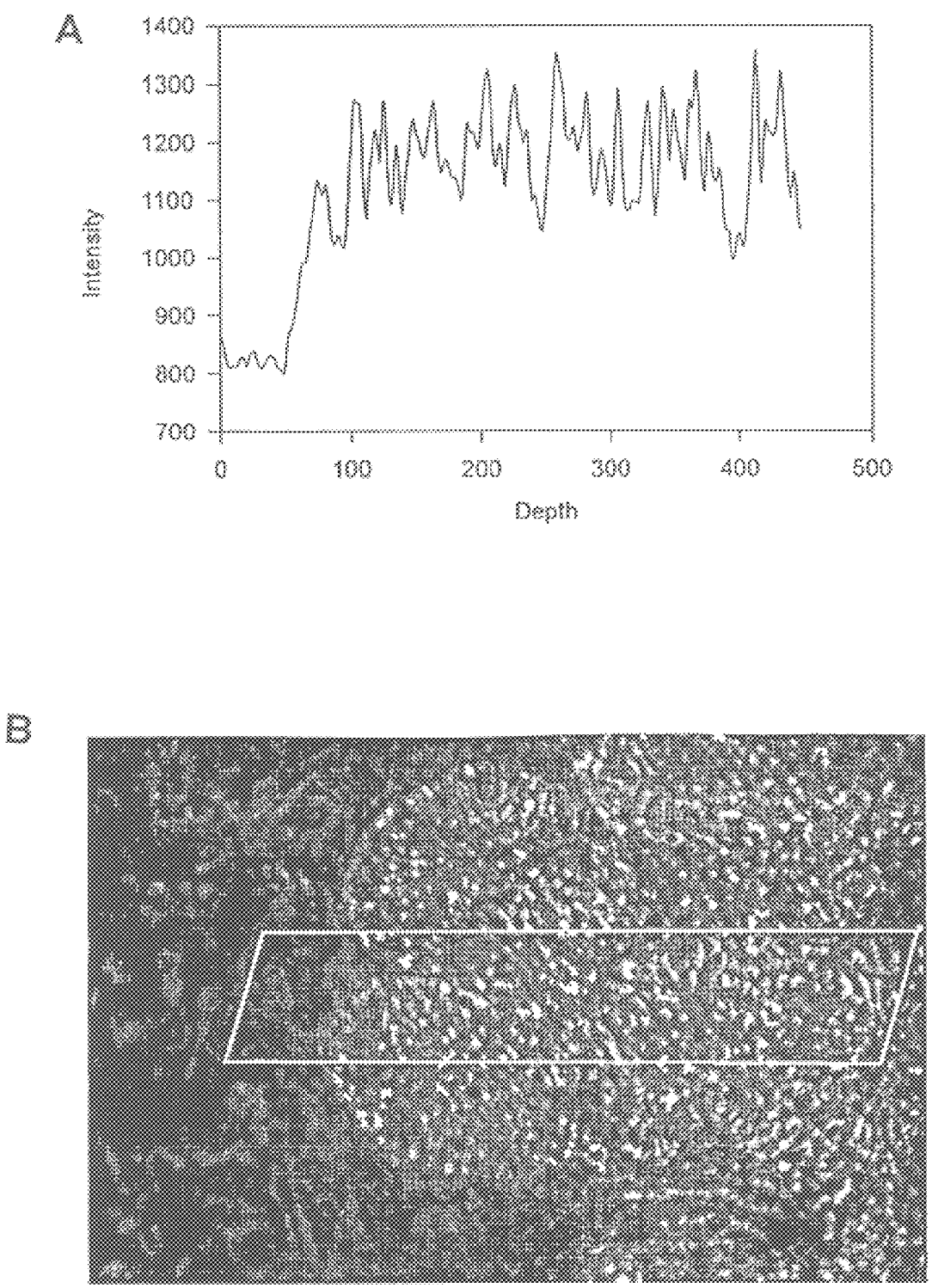
Figure 19:
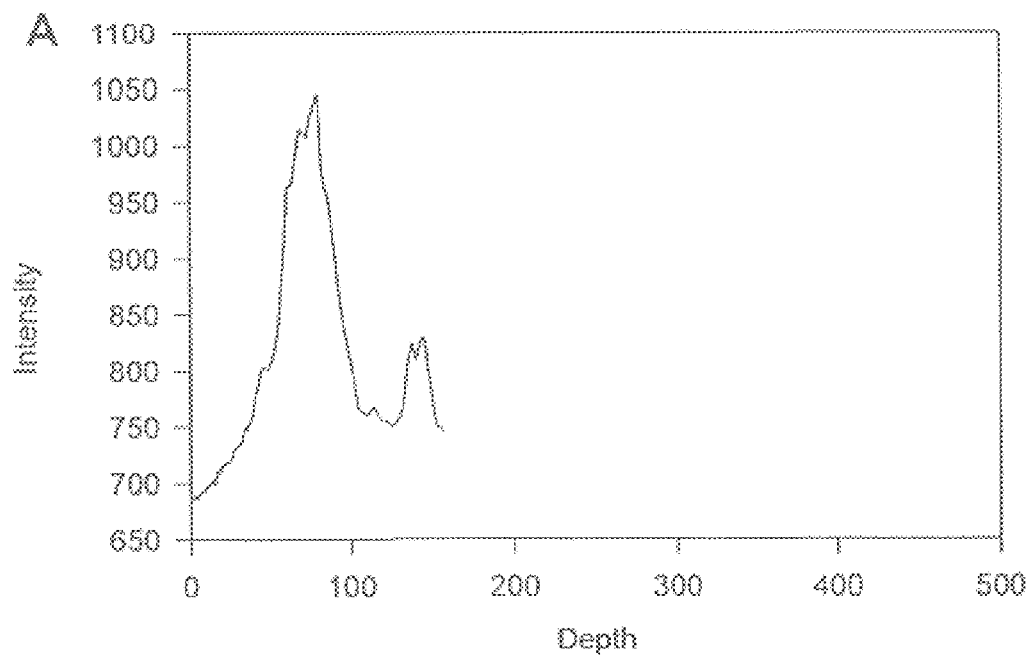
Figure 19:
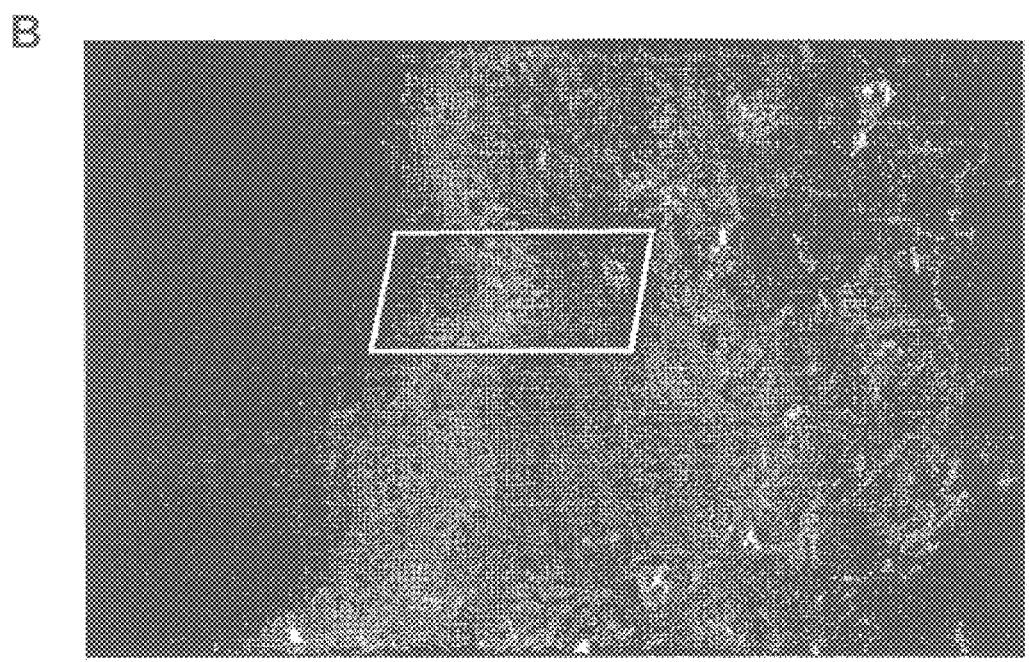

FIG. 12 shows measurement of PpIX production 4.5 hours following topical application of ALA methylester in human BCC by CDD microscopy of biopsies (A) graphical representation showing fluorescence intensity vs depth ($\mu$m) and (B) micrograph;

FIG. 13 shows measurement of PpIX production 4.5 hours following topical application of ALA methylester in human normal skin by CDD microscopy of biopsies (A) graphical representation showing fluorescence intensity vs depth ($\mu$m) and (B) micrograph;

FIG. 14 shows measurement of PPIX production 24 hours following topical application of ALA methylester in human BCC by CDD microscopy of biopsies (A) graphical representation showing fluorescence intensity vs depth ($\mu$m) and (B) micrograph;

FIG. 15 shows measurement of PpIX production 24 hours following topical application of ALA methylester in human normal skin by CDD microscopy of biopsies (A) graphical representation showing fluorescence intensity vs depth ($\mu$m) and (B) micrograph;

FIG. 16 shows measurement of PPIX production 24 hours following topical application of free ALA in human BCC by CDD microscopy of biopsies (A) graphical representation showing fluorescence intensity vs depth ($\mu$m) and (B) micrograph;

FIG. 17 shows measurement of PpIX production 24 hours following topical application of free ALA in human normal skin by CDD microscopy of biopsies (A) graphical representation showing fluorescence intensity vs depth (ILm) and (B) micrograph;

FIG. 18 shows measurement of PPIX production 4.5 hours following topical application of free ALA and 20% DMSO in human BCC by CDD microscopy of biopsies (A) graphical representation showing fluorescence intensity vs depth ($\mu$m) and (B) micrograph;

FIG. 19 shows measurement of PPIX production 4.5 hours following topical application of free ALA and 20%

Figure 20:
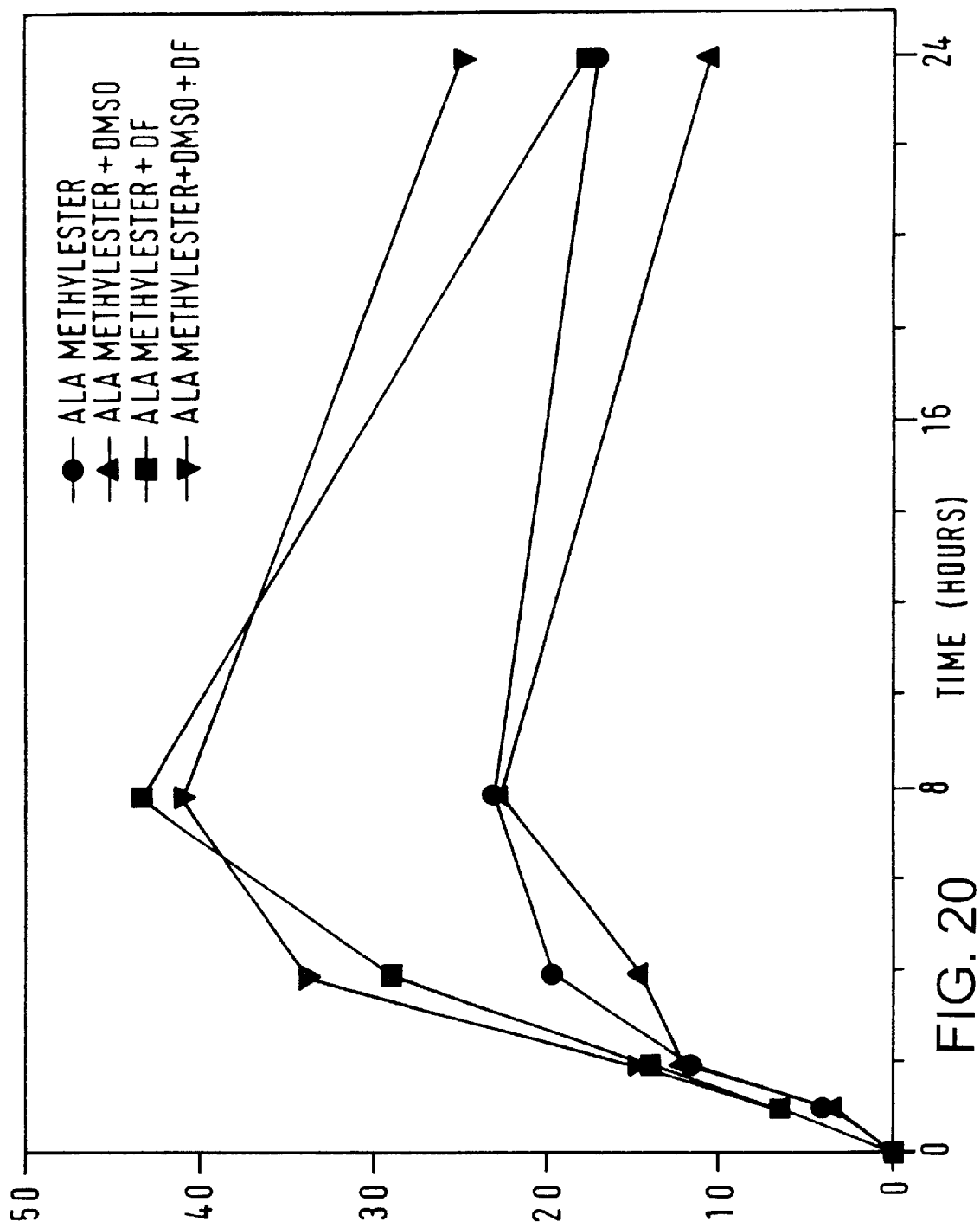
Figure 21:
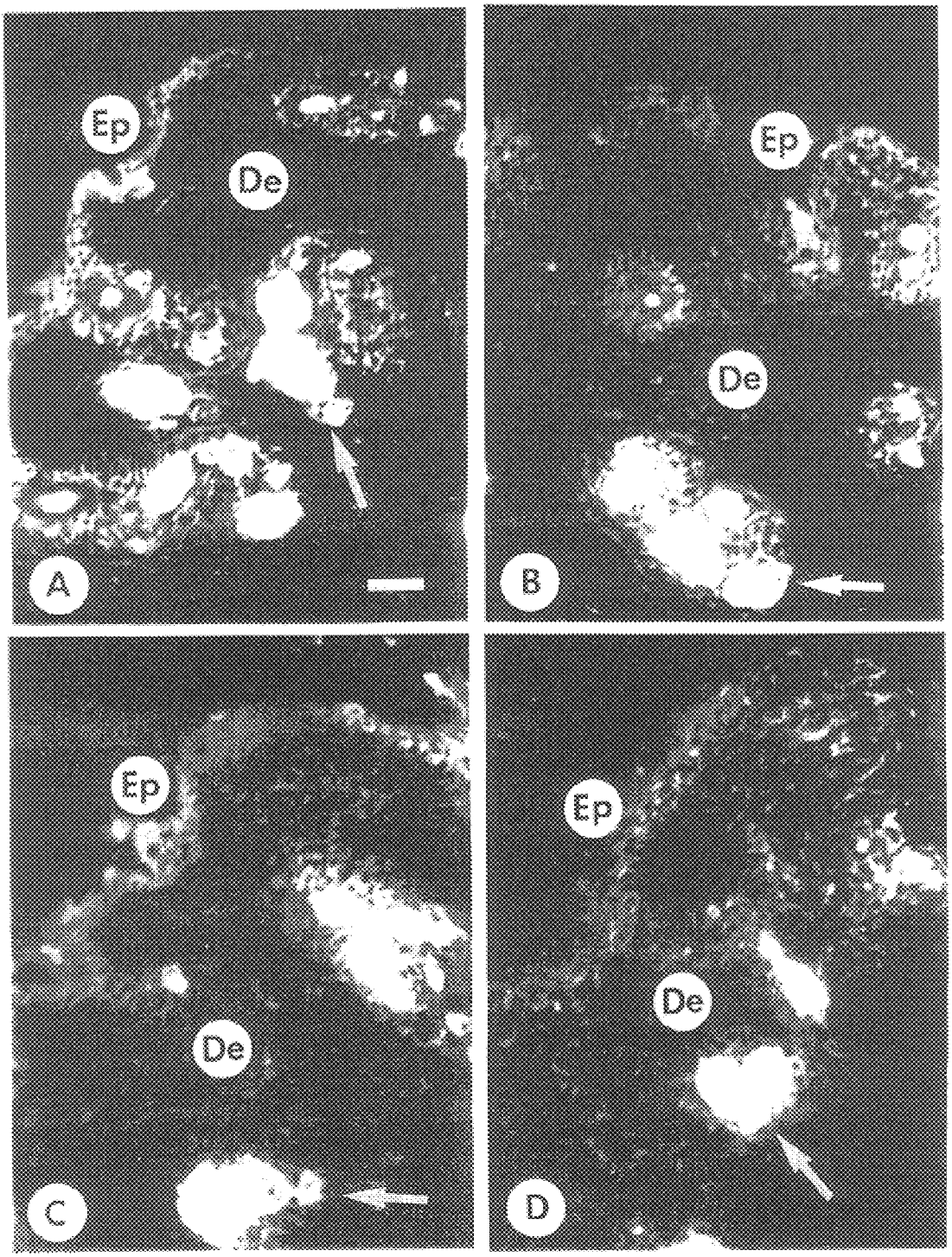

DMSO in human normal skin by CDD microscopy of biopsies (A) graphical representation showing fluorescence intensity vs depth ($\mu$m) and (B) micrograph;

FIG. 20 shows a time course (fluorescence intensity relative units vs time (hours)) of ALA methylesterinduced (PpIX) fluorescence in the mouse skin after topical application of ALA methylester alone (-●-), ALA methylester plus DMSO (-▲-), ALA methylester plus desferrioxamine (DF) (-■-) or ALA methylester plus DF and DMSO (-▼-). Each point is the mean of measurements from at least three mice;

FIG. 21 shows fluorescence photographs of the mouse skin taken 1 h after topical application of free ALA alone (A), ALA methylester (B), ALA ethylester (C) and ALA propylester (D), showing fluorescence in the epidermis (Ep), epithelial hair follicles and sebaceous gland (arrows), but not in the dermis (De). Original magnification ×250.

Figure 22:
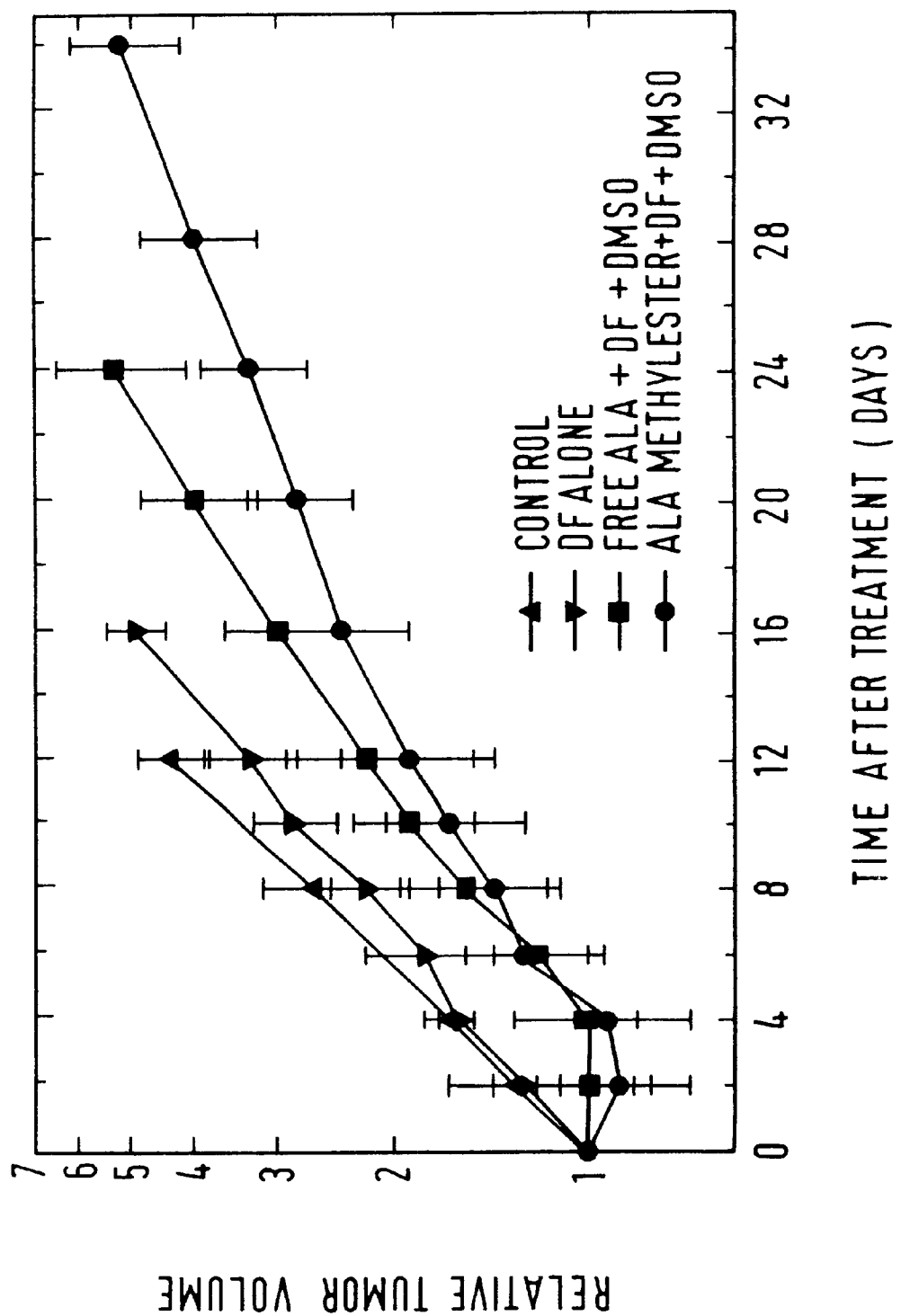

FIG. 22 is a graph showing relative tumour volume against time (days) following treatment of WiDr human colonic carcinoma transplanted subcutaneously into nude mice with ALA or ALA methylester plus DF; (-▲-) control; (-▼-) DF alone; (-■-) ALA+DF +DMSO; (-●-) ALA methylester+DF+DMSO.

Figure 23:
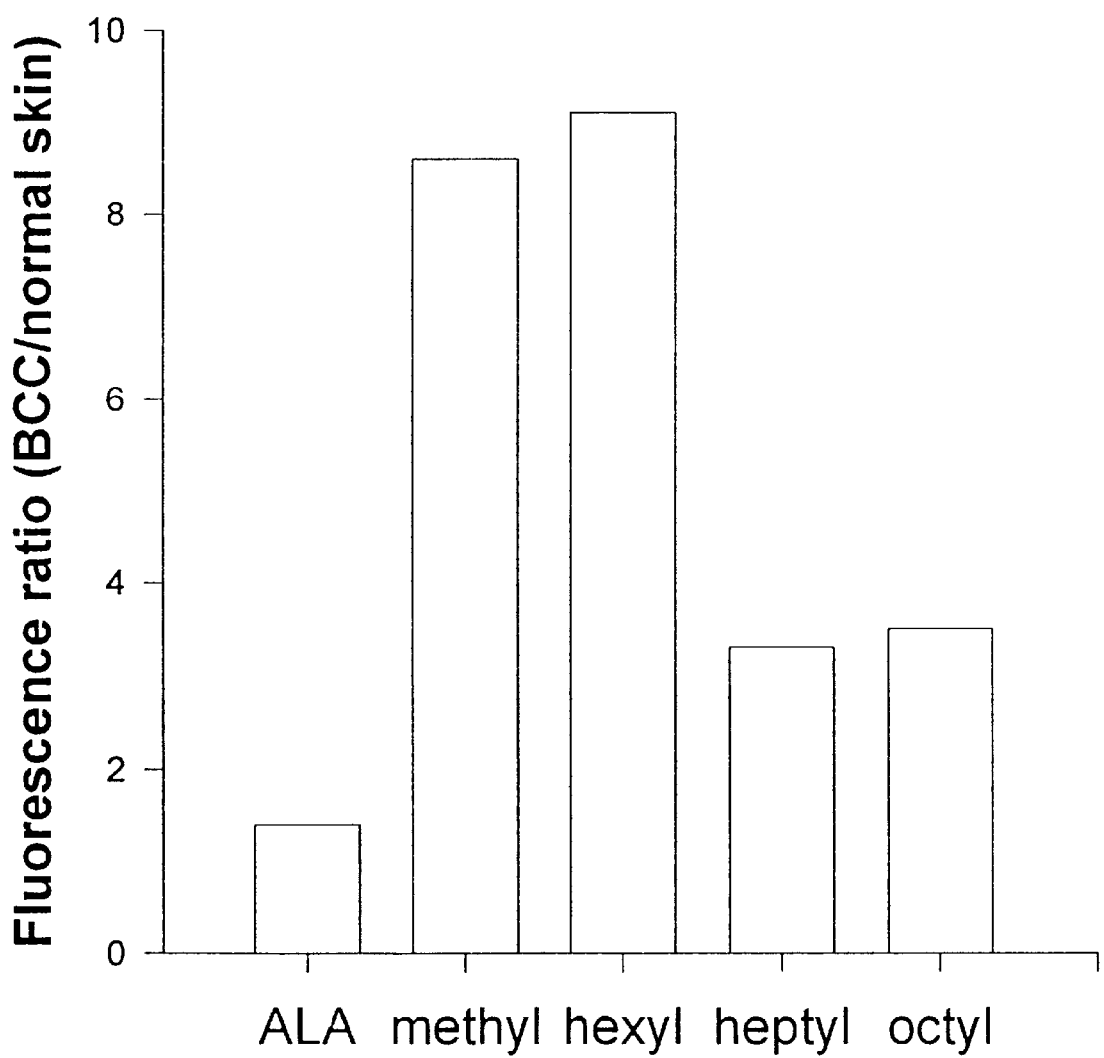

FIG. 23 shows PpIX fluoresence ratios between BCC lesions and surrounding normal skin after topical application of ALA or its esters.

EXAMPLE 1
Preparation of Methyl 5-Aminolevulinate Hydrochloride

To a 500 ml glass reactor containing 200 ml methanol, was added 1 g 5-amino-levulinic acid hydrochloride and 1 drop conc. HCl. The reaction mixture was then stirred overnight at 60° C. The progress of the esterification was followed by $^1$H-NMR. Excess methanol was removed by distillation, and the product further dried under vacuum at 30–40° C., giving methyl 5-aminolevulinate hydrochloride. The structure was confirmed by $^1$H-NMR in DMSO-$d_6$.

EXAMPLE 2
Preparation of Ethyl 5-Aminolevulinate Hydrochloride (ALA ethylester)

1 g 5-aminolevulinic acid hydrochloride was added to 200 ml dry ethanol containing 1–2 drops conc. hydrochloric acid in a 250 ml glass reactor equipped with a stirrer, reflux condenser and a thermometer. The esterification was performed at reflux overnight (70–80° C.). After the reaction had gone to completion, the ethanol was removed under vacuum. Finally, the product was dried under high vacuum at 30–40° C., giving 0.94 g Ethyl 5-aminolevulinate hydrochloride. Confirmation of the structure was done by $^1$H-NMR in DMSO-$d_6$.

EXAMPLE 3
Preparation of N-Propyl 5-Aminolevulinate Hydrochloride (ALA propylester)

0.5 g 5-aminolevulinic acid hydrochloride was dissolved in 100 ml dry n-propanol containing 1–2 drops of conc. hydrochloride in a 250 ml glass reactor equipped with a stirrer, reflux condenser and a thermometer. The reaction mixture was stirred at 70–80° C. for approx. 20 hours. After all the 5-aminoleviulinic acid was converted to its n-propylester (followed by $^1$H-NMR), the excess propanol was removed, and the product dried under high vacuum (<1 mBar) at 40–50° C. The reaction gave 0.49 g propyl 5-aminolevulinate hydrochloride. The structure was confirmed by $^1$H-NMR in DMSO-$d_6$.

EXAMPLE 4
Preparation of N-Hexyl 5-Aminolevulinic Hydrochloride (ALA Hexylester)

2 grams of 5-aminolevulinic acid hydrochloride was dissolved in 25 grams of dry n-hexanol with 5–6 drops of conc. hydrochloride added in a 50 ml glass reactor equipped with a reflux condenser and a thermometer. The reaction mixture was held at 50–60° C. for approx. 3 days. The excess n-hexanol was removed under vacuum and the product finally dried under high vacuum, giving 2.4 grams of n-hexyl 5-aminolevulinate hydrochloride. The structure was confirmed by $^1$H-NMR spectroscopy in DMSO-$d_6$.

EXAMPLE 5
Preparation of N-Heptyl 5-Aminolevulinic Hydrochloride (ALA Heptylester)

0.5 g 5-aminolevulinic acid hydrochloride was added to 30 grams of n-heptanol containing 5 drops of conc. hydrochloride in a 100 ml glass reactor equipped with a stirrer, reflux condenser and a thermometer. After all the 5-aminolevulinic acid had dissolved, the reaction mixture was stirred at 70–80° C. for approx. 48 hours. After the 5-aminolevulinic acid was converted to its n-heptyl ester (followed by $^1$H-NMR), the excess alcohol was removed, and the product dried under high vacuum (<1 mBar) at 70° C. The reaction gave 1.5 g n-heptyl 5-aminolevulinate hydrochloride. The structure was confirmed by $^1$H-NMR in DMSO-$d_6$.

EXAMPLE 6
Preparation of N-Octyl 5-Aminolevulinic Hydrochloride (ALA Octylester)

1 gram 5-aminolevulinic acid hydrochloride was added to 30 grams of dry n-octanol containing 5–6 drops of conc. hydrochloride in a 50 ml glass reactor equipped with a reflux condenser, stirrer and a thermometer. The reaction mixture was stirred at 65–70° C. for approx. 2 days. Excess n-octanol was removed under vacuum and the product finally dried under high vacuum, giving 1.5 grams of n-octyl 5-aminolevulinate hydrochloride. The structure was confirmed by $^1$H-NMR spectroscopy in DMSO-$d_6$.

EXAMPLE 7
Formulation

20% creams were prepared by admixture of the active component, ALA, ALA methylester, ALA ethylester, or ALA propylester (prepared according to Examples 1 to 3 respectively), with "Urguentum Merck" cream base (available from Merck) consisting of silicon dioxide, paraffin liq., vaseline, album, cetostearol., polysorbat. 40, glycerol monostearate, Miglyol®812 (a mixture of plant fatty acids), polypropyleneglycol., and purified water.

Corresponding creams were also prepared, additionally containing 3–20% DMSO.

EXAMPLE 8
Determination of Protoporohyrin IX Production in the Skin of Mice by CCD Microscopy of Biopsies:

A commercial oil-in-water cream containing (20% w/w) one of the chemicals (free ALA, ALA methylester, ALA ethylester and ALA propylester) (see Example 1) was topically applied to the normal skin of nu/nu nude mice for 0.5, 1, 3 and 6 hours, then biopsied and evaluated by means of microscopic fluorescence photometry incorporating a light-sensitive thermol-electrically cooled charge coupled device (CCD) camera. The results show that free ALA and its three ester derivatives are taken up by the skin tissue, the esterified ALA derivatives are being deesterified in the skin, and converted into protoporphyrin IX (PpIX) 0.5 hours after topical application. The fluorescence intensity of PpIX in the skin increased with the time of the application and the maximum amounts of the fluorescence were seen about 6 hours (the latest time point studied) after the application in all cases.

EXAMPLE 9
Measurements in situ of Protoporphyrin IX Production in the Skin of Mice by an Optical-Fiber Based System The aim of this study was to investigate the build-up of esterified ALA ester-induced porphyrins fluorescence in the normal skin of nude mice in vivo after topical or systemic administration of ALA ester derivatives.

Materials and Methods
Chemicals.

5-aminolevulinic acid (ALA) methyl-, ethyl- and propyl-esters ($H_2N-CH_2COOCH_2-CH_2COO-R$; R can be $CH_3$, $CH_2-CH_2-CH_3$) were prepared by Norsk Hydro Research Center (Porsgrunn, Norway) as described in Examples 1 to 3. Free ALA hydrochloride and desferrioxamine mesylate (DF) were purchased from Sigma Chemical Company (St. Louis, Mo., USA). Dimethyl sulphoxide (DMSO) was obtained from Janssen Chimica (Geel, Belgium). Commercial oil-water creams (Unguentum Merck, Darmstadt, Germany) containing 20% one of the ALA ester derivatives (w/w), 20% free ALA, 20% ALA methylester plus 5% DF, 20% ALA methylester plus 20% DMSO, or 20% ALA methylester plus 5% DF and 20% DMSO were freshly prepared prior to use. All creams were made by the Pharmacy at the Norwegian radium Hospital. For intraperitoneal injection, ALA and its methylester were freshly dissolved in saline. All other chemicals used were of the highest purity commercially available.

Animals.

Female Balb/c nu/nu athymic nude mice were obtained from the Animal Laboratory at the Norwegian Radium Hospital and kept under specific-pathogen-free conditions. At the start of the experiments the mice were 6–7 weeks old weighing 18–24 g. Three mice were housed per cage with autoclaved covers in a dark room during the experiments.

Treatment Procedure.

One of the creams was painted on the normal skin at right flank region of each mouse, and covered by a semi-permeable dressing (3M, St Paul, Minn., USA) for various time intervals (from 0.25 to 24 h) before fluorescence measurements in situ or being biopsied for microscopic fluorescence imaging. About 0.2 g cream was applied to an approximate 2.25 $cm^2$ area of the skin. In the case of i.p. injection the mice were given ALA or its methylester at a dose of 150 mg/kg. At least three mice were used for each condition.

Fluorescence Spectroscopic Measurements in situ.

A perkin Elmer LS-50 fluorescence spectrometer equipped with a red-sensitive photomultiplier (Hamamatsu R 928) was used. This instrument has a pulsed Xenon arc light source and phase sensitive detection, such that fluorescence can be readily measured. Part of the excitation beam (set at 408 nm for fluorescence measurements) was reflected into a 600 $\mu$m core multimodus optical quartz fiber (No. 3501 393, Dornier Medizintechnik, GmbH, Germering, Germany) by means of a mirror for application onto the subject through a hand held probe. Emission in the region of 550–750 nm was measured via emission fibres collecting information through the probe.

Fluorescence Microscopy.

After the creams were topically applied to the skin of mice for various times (as indicated above), the skin was biopsied and the frozen tissue sections were cut with a cryostat to a thickness of 8 $\mu$m. The fluorescence microscopy was carried out using an Axioplan microscope (Zeiss, Germany) with a 100 W mercury lamp. The fluorescence images were recorded by a light-sensitive thermoelectrically cooled charge coupled device (CCD) camera (resolution: 385×578 pixels with a dynamic range of 16 bits per pixel)(Astromed CCD 3200, Cambridge, UK) and hard copies on a video printer (Sony multiscan video printer UP-930). The filter combination used for detection of porphyrin fluorescence consisted of 390–440 nm excitation filter, a 460 nm beam splitter and a >600 nm emission filter.

Results

Figure 1:
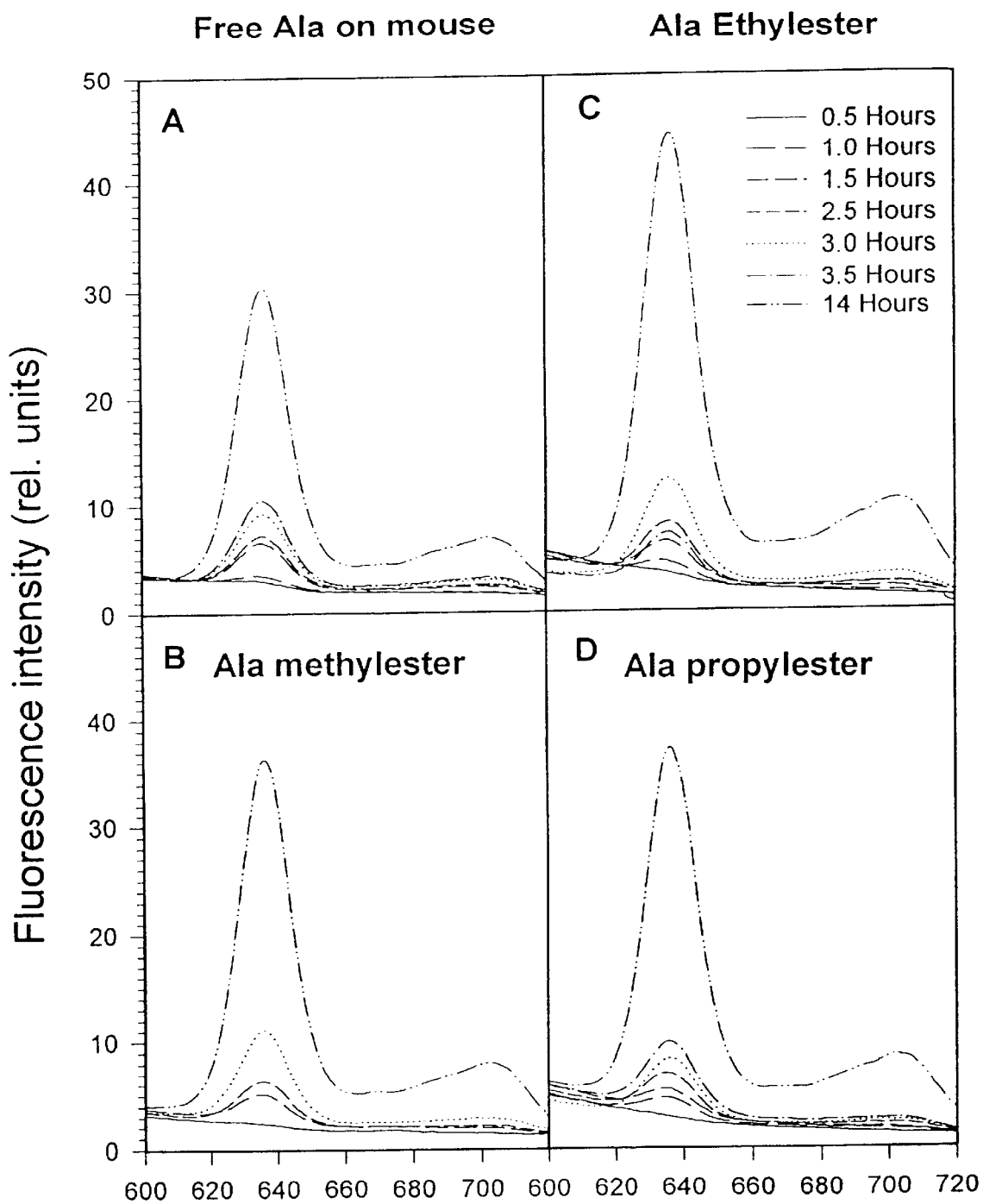
FIG. 1 shows fluorescence intensity (relative units vs wavelength (nm)) of PpIX in the normal skin of mice after topical administration of (A) free ALA
(B) ALA methylester
(C) ALA ethylester
(D) ALA propylester after 0.5, 1, 1.5, 2.5, 3, 3.5 and 14 hours following administration.
Figure 2:
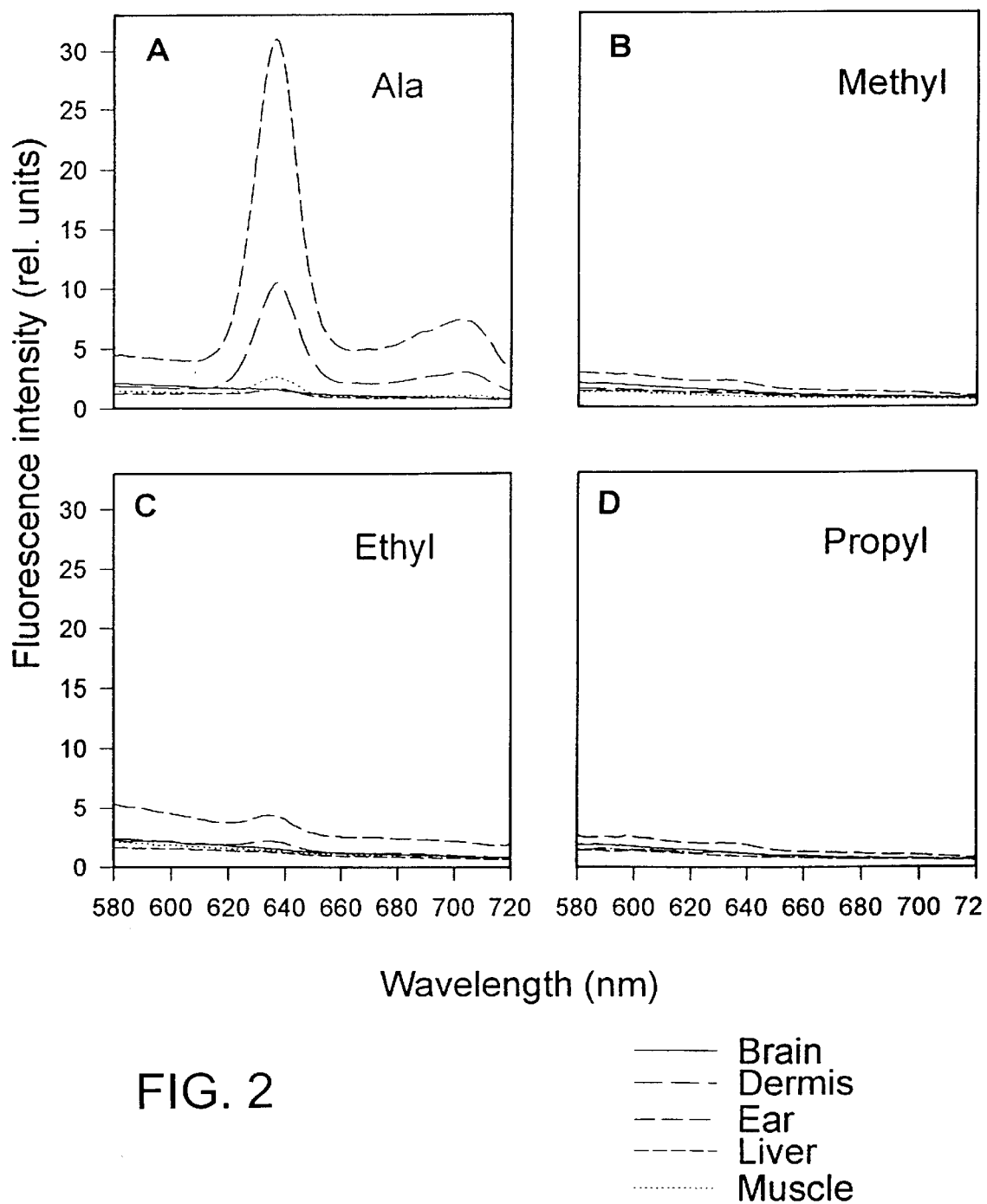
FIG. 2 shows the distribution of PpIX as measured by fluorescence intensity (relative units vs wavelength (nm)) in Brain, dermis, Ear, Liver and muscle 14 hours after topical administration to the normal skin of mice.

PpIX fluorescence was measured in situ by an optical-fiber based system in the normal skin of nude mice 0.5, 1, 1.5, 2.5, 3, 3.5 and 14 hours after topical application of free ALA or one of its ester derivatives as described above. As shown in FIG. 1, the pPIX fluorescence was already built-up 1 hour after topical application in the case of all derivatives, while the fluorescence was seen 1.5 hours after the application of free ALA. The maximum fluorescence intensity was found 14 hours after the application in all cases, but PpIX fluorescence induced from ALA esters in the skin was stronger than that from free ALA. Furthermore, as can be seen in FIG. 2, 14 hours after the application no fluorescence of ALA-esters-induced PpIX was detected in other areas of the skin and internal organs including ear, dermis, muscle, brain and liver. However, in the case of free ALA, a strong fluorescence was also seen in the ear as well as in the other areas of the skin. Thus, after topical application ALA-ester-induced PpIX was found locally in the skin, whereas free ALA-induced PpIX distributed not only locally, but also in other areas of the skin. We suggest that ALA is transported in the blood and that PpIX is subsequently formed in all organs containing the enzymes of the heme synthesis pathway and/or PPIX is formed in the skin and then transported to other tissues via blood circulation. The latter situation may lead to skin photosensitivity in areas where free ALA is not topically applied. In addition, after intraperitoneal injection of ALA methylester at a dose of 150 mg/kg, the PPIX fluorescence in the skin of mice was built-up 15 minutes after the injection and the peak value was found around 4 hours, and the fluorescence disappeared within 10 hours post the injection (FIG. 3). This kinetic pattern is similar to that of the fluorescence of free ALA-induced porphyrins in the skin following i.p. injection of the same dose, although the fluorescence decreased faster in the case of the ester than in the case of the free ALA.

EXAMPLE 10
Measurements of Protoporphyrin IX Production in Human Basal Cell Carcinoma (BCC) and Surrounding Normal Skin by Optical-Fiber Based System The PpIX fluorescence in the BCC lesions and surrounding normal skin of human patients was measured in situ by optical-fiber based system after topical application of 20% free ALA and its derivatives for various time intervals.

FIGS. 4, 5, 6 and 7 show that, compared to free ALA, the ALA derivatives-induced PpIX was built up faster, produced more and localized more selectively in the BCC lesions (i.e. much less fluorescence in the surrounding normal skin), particularly for ALA methylester.

EXAMPLE 11
In vivo Fluorescence Surface Measurements of PpIX Production in Human BCC and Surrounding Normal Skin by CCD Microscopy of Biopsies In a 78 years old Caucasian male presenting multiple ulcero-nodular BCCs lesions were exposed to commercial oil-in-water creams containing either ALA alone (20% w/w) or ALA methyl ester (20% w/w) (as described in Example 7) covered by a semi-permeable dressing for 24 hours. After removal of dressings and cream in vivo fluorescence was measured at the surface of tumor tissue and adjacent normal skin by means of a spectrofluorometer. Punch biopsies of the same areas were removed and samples were immediately immersed in liquid nitrogen. The tissue sections were cut with a cryostat microtome to a thickness of 8 µm. The localization pattern of the porphyrin fluorescence in the tissue sections was directly observed by means of fluorescence microscopy. The same frozen sections were subsequently stained with routine H&E staining for histological identification. The same sections were subsequently stained with routine H&E staining for histological identification. Fluorescence microscopy was carried out with an Axioplan microscope (Zeiss, Germany). Fluorescence images and quantitative measurements were performed by a light-sensitive thermol-electrically cooled charge coupled device (CCD) camera (Astromed CCD 3200, Cambridge, UK) and an image processing unit (Astromed/Visilog, PC 486DX2 66 MHz VL). The main purpose for such quantitative measurements is to determine the exact penetration of ALA-induced porphyrins from tissue surface to the bottom layers of cancer lesions. The results are shown in FIGS. 8 and 9 in which the fluorescence intensity is expressed as a function of depth of cancer lesion.

As shown in FIGS. 8 and 9, an homogeneous distribution of PpIX fluorescence is seen from the top to the bottom of the whole BCC lesions after use of either free ALA or its methyl ester. This suggests that ALA methylester is at least as good as free ALA in terms of penetration and PpIX production in the BCC lesion. In addition, no PPIX fluorescence was seen in the surrounding normal skin after topical application of ALA methylester, indicating that ALA-methylester-induced PpIX highly selectively took place only in the BCC lesion.

In vivo fluorescence after 24 hours showed at least doubled fluorescence intensity for ALA methyl ester compared to ALA for the selected tumors and also an increase for corresponding normal tissues, however this only of about 50%. The ratio between tumor and normal tissue was about 1.2:1 for ALA and 2:1 for the ALA methyl ester. The results are shown in FIGS. 10 and 11.

At control one week after treatment all treatment fields presented a central necrotic area corresponding to the tumor. In the adjacent normal skin exposed to cream and light irradiation there was observed a marked erythema for the ALA while for the ALA methyl ester only moderate erythema was observed.

EXAMPLE 12
In Vivo Fluorescence Surface Measurements of IX Production in Human BCC and Surrounding Normal Skin by CCD Micrscopy of Biopsies The present data show the localization patterns and production of porphyrins (mainly protoporphyrin IX (PpIX)) after topical application of free ALA and one of its derivatives (methyl ester) for 4.5 and 24 hours in the nodular basal cell carcinomas (BCCs) and surrounding normal skin of patients. The tests were performed as described in Example 11.

Each of the following figures show both (A) fluorescence images of either the bottom layer of BCC lesions or of the surrounding normal skin. Curves indicating the fluorescence intensity as a function of depth of the BCC lesions or of the normal skin are also shown (B).

FIG. 12 shows a homogenous distribution of PpIX fluorescence generated by ALA methyl ester in the bottom layer of a BCC 4.5 hours after topical application. There is also some porphyrin fluorescence in surrounding normal skin (FIG. 13). The fluorescence intensity ratio between BCC and the normal skin is about 2. Moreover, the absolute amount of the fluorescence induced by ALA methyl ester is higher than that induced by free ALA and 20% DMSO after topical application for 4.5 hours, as shown below.

FIGS. 14 and 15 show a uniform distribution of porphyrin fluorescence induced by topical application of ALA methyl ester for 24 hours in the bottom layer of BCC and surrounding normal skin. The ratio of the fluorescence in BCC and that in normal skin is also about 2. Furthermore, the fluorescence intensity of ALA methyl ester-induced porphyrins in the BCC is almost twice as high as that in BCC after topical application of free ALA alone for 24 hours, as shown below.

FIGS. 16 and 17 show a homogenous distribution of free ALA-induced porphyrins in the bottom layer of BCC and surrounding normal skin 24 following topical application. However, the ratio of the fluorescence intensity between BCC and normal skin is about 1, which indicates a low selectivity of this treatment. Moreover the production of porphyrins in BCC is less than that in the case of ALA methyl ester.

FIGS. 18 and 19 show a homogenous distribution of ALA-induced porphyrins in the bottom layer of BCC and surrounding normal skin after topical application of free ALA and 20% DMSO for 4.5 hours. However, the ratio of the fluorescence intensity between BCC and normal skin is only slightly larger than 1, which demonstrates that the DMSO probably reduces the tumor selectivity of the porphyrins produced. Moreover, also in this case less porphyrins are produced in BCC than in the case of the application of ALA methyl ester.

EXAMPLE 13
Investigation of the Effects of the Chelating Agent Desferrioxamine (DF) and/or DMSO and Fluorescence of Skin I. The effect of DF and/or DMSO on the build up of fluorescence in the normal skin of mice in situ was ascertained various times after topical administration of ALA-methylester. Methods were performed as described in Example 9.

Results

Topical application of the cream alone containing only DMSO did not show any fluorescence in the normal mouse skin, but there was some fluorescence of PPIX after DF alone was applied.

DF or DF plus DMSO (a well-known skin penetration enhancer) significantly enhanced the production of ALA methylester-induced PpIX.

II. Fluorescence imaging of the skin treated with three derivatives (performed as described in Example 9) showed fluorescence of the ester derivative-induced porphyrins in the epidermis, epithelial hair follicles and sebaceous glands 1 h after topical application (FIG. 21). The fluorescence intensity of the porphyrins increased with the time after the application.

Summary

A large number of patients with basal cell carcinomas (BCCs) has topically been treated with ALA-based PDT in our hospital during the past five years and more than 90% of superficial BCCs have shown a complete regression. However, nodular BCCs had a low complete response rate due to a poor ALA retention and, consequently, a low ALA-induced porphyrin production in the deep layers of the lesions. In order to improve the technique, we used ALA ester derivatives instead of free ALA. The present data obtained presented in this Example and in Example 9 by means of both fluorescence spectroscopic measurements in situ and fluorescence microscopy of tissue biopsies, indicate that all three ester derivatives studied were taken up, de-esterified and finally converted into porphyrins in the epidermis, epithelial hair follicles and sebaceous glands of the nude mice with a higher porphyrin production than that of free ALA. This is in agreement with the preceding Examples concerning a study of human nodular basal cell carcinoma that demonstrate that the fluorescence of the ALA ester-induced porphyrins was built up faster with a higher intensity and a more homogenous distribution than those of free ALA-induced porphyrins in the lesions.

The present study also shows that DF has a significant effect in enhancing the production of ALA methylesterderived PpIX in the normal skin of the mice after topical application.

Interestingly, a strong fluorescence of free ALA-induced porphyrins was found in regions of the skin outside the area where the cream was topically applied (FIG. 2). This indicates that after topical application free ALA is transported in the blood and porphyrins are subsequently formed in all organs containing the enzymes of the heme synthesis pathway or porphyrins are initially formed in the skin or/and liver, then transported to other tissues via blood circulation. This may lead to skin photosensitivity in areas where free ALA is even not topically applied. However, none of the ester derivatives studied induced porphyrin fluorescence in other parts of the skin.

EXAMPLE 14
Effects of ALA Methylester or ALA, DF and DMSO PDT on Tumor Growth in WiDr Human Colonic Carcinoma-Transplanted Nude Mice Nude mice were transplanted with WiDr human colonic carcinoma cells by subcutaneous injection into the right flank region. The following creams, formulated as described in the preceding Examples, were applied topically to the site of the tumor: 10% DF alone; 20% ALA+10% DF+20% DMSO; or 20% ALA methylester+10% DF+20% DMSO, followed, 14 hours later by laser light irradiation (632 nm, 150 mW/cm$^2$ for 15 minutes). A separate group of animals bearing the same tumor model, but receiving no topical application of the cream, served as a control. The responses of the treated tumors were evaluated as tumor regression/regrowth time. When the tumors reached a volume 5 times that of the volume on the day of light irradiation, the mice were killed. The results are shown in FIG. 22. (Bars: standard error of mean (SEM) based on 3–5 individual animals in each group). The results show that it took 34 days for tumors treated with ALA methylester+DF+DMSO to reach a volume five times that of the volume on the day just before light irradiation, whereas in the case of free ALA+DF+DMSO it took 24 days for the treated tumors to grow to 5 times size. Thus, ALA methylester is more effective than ALA in slowing tumor regrowth.

EXAMPLE 15
Selectivity of ALA Esters (Methyl, Hexyl, Heptyl and Octyl) for Non-Normal Tissue The PpIX fluorescence ratios between BCC lesions and surrounding normal skin after topical application of ALA or its esters (20% for 4 hours), was examined using methods described in previous examples. The results are shown in FIG. 23 and indicate that all esters can more selectively induce PpIX in BCC lesions than free ALA, particularly in the case of ALA-methylester and ALAhexylester.

What is claimed is:

1. A method for the diagnosis or photochemotherapeutic treatment of infections or skin disorders of the body, comprising:

i) administering to the sites of investigation or affected surfaces of the body a composition comprising a compound of formula I $$R_2^2N\text{—}CH_2COCH_2\text{—}CH_2CO\text{—}OR^1 \qquad (I)$$

wherein $R^1$ is alkyl; and each $R^2$ is independently hydrogen or alkyl; wherein each alkyl of $R^1$ and $R^2$ is optionally substituted by hydroxy, alkoxy, acyloxy, alkoxycarbonyloxy, amino, aryl, oxo or fluoro groups and is optionally interrupted by oxygen atoms; or a salt thereof; and ii) exposing said sites or surfaces to light.

2. The method of claim 1 wherein aryl is phenyl or a monocyclic 5–7 membered heteroaromatic.

3. The method of claim 1 wherein $R^1$ represents an unsubstituted alkyl group and each $R^2$ is hydrogen.

4. The method of claim 1 wherein $R^1$ represents an unsubstituted alkyl group or each $R^2$ is hydrogen.

5. The method of claim 1 wherein alkyl contains up to 10 carbon atoms.

6. The method of claim 1 wherein the compound is ALA-methyl ester, ALA-ethyl ester, ALA-propyl ester, ALA-hexyl ester, ALA-heptyl ester, or ALA-octyl ester; or a salt thereof.

7. The method of claim 1 wherein the light is in the wavelength region 500–700 nm.

8. The method of claim 1 wherein the skin disorder is psoriasis.

9. The method of claim 1 wherein the infection is a bacterial, viral or fungal infection.

* * * * *